(12) United States Patent
Pellegrino et al.

(10) Patent No.: US 6,736,835 B2
(45) Date of Patent: May 18, 2004

(54) EARLY INTERVENTION SPINAL TREATMENT METHODS AND DEVICES FOR USE THEREIN

(75) Inventors: Richard C. Pellegrino, Mendon, MA (US); Martin Reynolds, Mansfield, MA (US)

(73) Assignee: DePuy Acromed, Inc., Raynham, MA (US)

( * ) Notice: Subject to any disclaimer, the term of this patent is extended or adjusted under 35 U.S.C. 154(b) by 0 days.

(21) Appl. No.: 10/103,439

(22) Filed: Mar. 21, 2002

(65) Prior Publication Data

US 2003/0181963 A1 Sep. 25, 2003

(51) Int. Cl.$^7$ ............................................. A61F 7/00
(52) U.S. Cl. ........................... 607/96; 607/101; 601/2
(58) Field of Search ..................... 601/2–3; 606/41, 606/42, 48–50; 607/96, 98, 99, 101–102

(56) References Cited

U.S. PATENT DOCUMENTS

| | | |
|---|---|---|
| 4,312,364 A | 1/1982 | Convert |
| 4,448,198 A | 5/1984 | Turner |
| 4,573,448 A | 3/1986 | Kambin |
| 4,679,561 A | 7/1987 | Doss |
| 5,084,043 A | 1/1992 | Hertzmann et al. |
| 5,201,729 A | 4/1993 | Hertzmann et al. |
| 5,366,443 A | 11/1994 | Eggers et al. |
| 5,374,265 A | 12/1994 | Sand |
| 5,391,197 A | 2/1995 | Burdette et al. |
| 5,433,739 A | 7/1995 | Sluijter et al. |
| 5,437,661 A | 8/1995 | Rieser |
| 5,458,596 A | 10/1995 | Lax et al. |
| 5,458,597 A | 10/1995 | Edwards et al. |
| 5,472,441 A | 12/1995 | Edwards et al. |
| 5,484,432 A | 1/1996 | Sand |
| 5,514,130 A | 5/1996 | Baker |

(List continued on next page.)

FOREIGN PATENT DOCUMENTS

| | | | |
|---|---|---|---|
| EP | 0 597 463 A2 | 5/1994 | |
| EP | 1 059 067 A1 | 12/2000 | |
| JP | 2001037760 A | * 2/2001 | ............ A61B/8/12 |
| WO | 43 26 037 | 2/1995 | |
| WO | WO 02/05699 | 1/2002 | |
| WO | WO 02/096304 | 12/2002 | |

OTHER PUBLICATIONS

Kleinstueck, Frank S. et al.; Acute Biomechanical and Histological Effects of Indtradiscal Electrothermal Therapy on Human Lumbar Discs; SPINE vol. 26, No. 20, pp 2198–2207; 2001, Lippincott Williams & Wilkins, Inc.

Tillotson, Christopher L et al.; Controlled Thermal Injury of Bone Report of a Percutaneous Technique Using Radiofrequency Electrode and Generator; Investigative Radiology Nov. 1989 vol. 24, pp 888–892.

(List continued on next page.)

Primary Examiner—Roy D. Gibson

(57) ABSTRACT

There is provided a device for therapeutically treating back or leg pain, comprising:
  a) a probe having a proximal portion and a distal portion,
  b) first and second treatment sources, each source located in the distal portion of the probe,
wherein the first treatment source is adapted to therapeutically treat a first tissue site, the second treatment source is adapted to therapeutically treat a second different tissue site, and
wherein the first and second different tissue sites are selected from the group consisting of:
  i) a first intervertebral disc,
  ii) a first vertebra,
  iii) a first spinal ligament, and
  iv) a first spinal facet joint capsule,
  v) a second intervertebral disc,
  vi) a second vertebra,
  vii) a second spinal ligament, and
  viii) a second spinal facet joint capsule.

76 Claims, 14 Drawing Sheets

U.S. PATENT DOCUMENTS

| | | | |
|---|---|---|---|
| 5,569,242 A | 10/1996 | Lax et al. | |
| 5,620,479 A | 4/1997 | Diederich | |
| 5,630,426 A | 5/1997 | Eggers et al. | |
| 5,630,837 A | 5/1997 | Crowley | |
| 5,697,281 A | 12/1997 | Eggers et al. | |
| 5,720,287 A * | 2/1998 | Chapelon et al. | 600/439 |
| 5,733,315 A | 3/1998 | Burdette et al. | |
| 5,743,904 A | 4/1998 | Edwards | |
| 5,752,969 A | 5/1998 | Cunci et al. | |
| 5,762,066 A | 6/1998 | Law et al. | |
| 5,776,092 A | 7/1998 | Farin et al. | |
| 5,785,705 A | 7/1998 | Baker | |
| 5,800,378 A | 9/1998 | Edwards et al. | |
| 5,807,392 A | 9/1998 | Eggers | |
| 5,810,764 A | 9/1998 | Eggers et al. | |
| 5,817,021 A * | 10/1998 | Reichenberger | 600/439 |
| 5,843,019 A | 12/1998 | Eggers et al. | |
| 5,843,021 A | 12/1998 | Edwards et al. | |
| 5,855,576 A | 1/1999 | LeVeen et al. | |
| 5,865,788 A | 2/1999 | Edwards et al. | |
| 5,868,740 A | 2/1999 | LeVeen et al. | |
| 5,871,481 A | 2/1999 | Kannenberg et al. | |
| 5,873,877 A | 2/1999 | McGaffigan et al. | |
| 5,895,370 A | 4/1999 | Edwards et al. | |
| 5,902,272 A | 5/1999 | Eggers et al. | |
| 5,904,681 A | 5/1999 | West, Jr. | |
| 5,954,716 A | 9/1999 | Sharkey et al. | |
| 5,964,727 A | 10/1999 | Edwards et al. | |
| 6,007,570 A | 12/1999 | Sharkey et al. | |
| 6,022,334 A | 2/2000 | Edwards et al. | |
| 6,053,909 A * | 4/2000 | Shadduck | 606/3 |
| 6,073,051 A | 6/2000 | Sharkey et al. | |
| 6,095,149 A | 8/2000 | Sharkey et al. | |
| 6,099,514 A | 8/2000 | Sharkey et al. | |
| 6,228,046 B1 * | 5/2001 | Brisken | 604/22 |
| 6,235,024 B1 * | 5/2001 | Tu | 606/41 |
| 6,261,311 B1 | 7/2001 | Sharkey et al. | |
| 6,290,715 B1 | 9/2001 | Sharkey et al. | |
| 6,436,060 B1 * | 8/2002 | Talish | 601/2 |
| 6,451,013 B1 * | 9/2002 | Bays et al. | 606/27 |
| 6,527,759 B1 * | 3/2003 | Tachibana et al. | 604/500 |
| 6,585,656 B2 * | 7/2003 | Masters | 600/466 |
| 2001/0023348 A1 * | 9/2001 | Ashley et al. | 606/41 |
| 2001/0029370 A1 * | 10/2001 | Hodva et al. | 606/41 |
| 2002/0019626 A1 | 2/2002 | Sharkey et al. | |

OTHER PUBLICATIONS

Heggeness, Michael H. et al., Discography Causes End Plate Deflection; SPINE vol. 18, No. 8, pp 1050–1053, 1993, J.B. Lippincott Company.

Letcher, Frank S. et al.; The Effect of Radiofrequency Current and Heat on Peripheral Nerve Action Potential in the Cat;; U.S. Naval Hospital, Philadelphia, PA.

Houpt, Jonathan C. et al.; Experimental Study of Temperature Distributions and Thermal Transport During Radiofrequency Current Therapy of the Intervertebral Disc; SPINE vol. 21, No. 15, pp 1808–1813, 1996, Lippincott–Raven Publishers.

Lundskog, Jan; Heat and Bone Tissue—/an experimental investigation of the thermal properties of bone tissue and threshold levels for thermal injury; Sandinavian Journal of Plastic and Reconstructive Surgery Supplemental 9, From the Laboratory of Experimental Biology, Department of anatomy, University of Gothenburg, Gothenburg, Sweden, GOTEBORG 1972.

Antonacci, M. Darryl et al.; Innervationof the Human Vertebral Body: A Histologic Study; Journal of Spinal Disorder, Vol 11, No. 6, pp. 526–531, 1998 Lippincott Williams & Wilkins, Philadelphia.

Arnoldi, Carl C.; Intraosseous Hypertension—A Possible Cause of Low Back Pain?; Clinical Orthopedics and Related Research, No. 115, Mar.–Apr., 1976.

Esses, Stephen I. et al.; Intraosseous Vertebral Body Pressures; SPINE vol. 17 No. 6 Supplement 1992.

Sherman, Mary S., The Nerves of Bone; The Journal of Bone and Joint Surgery; Vol 45–A, No. 8, Apr. 1963.

Troussier, B. et al.; Percutaneous Intradiscal Radio–Frequency Thermocoagulation A Cadaveric Study; SPINE vol. 20, No. 15, pp 1713–1718, 1995, Lippincott–Raven Publishers.

Choy, Daniel SS.J. et al.; Percutaneous Laser Disc Decompression, A New Therapeutic Modality; SPINE vol. 17 No. 8 1992.

Shealy, C. Norman; Percutaneous radiofrequency denervation of spanal facets Treatment for chronic back pain and sciatica; Journal of Neurosurgery/vol. 43/Oct. 1975.

Depuy, Damian E.; Radiofrequency Ablation: An Outpaitent Percutaneous Treatment; Medicine and Health/Rhode Island vol. 82 No. 6 Jun. 1999.

Rashbaum, Ralph F.; Ratiofrequency Facet Denervation A Treatment alternative in Refractory Low back Pain with or without Leg Pain; Orthopedic Clinics of North America–vol. 14, No. 3, Jul. 1983.

Lehmann, Justus F. et al.; Selective Heating Effects of Ultrasound in Human Beings; Archives of Physical Medicine & Rehabilitation Jun., 1966.

Hanai, Kenji et al.; Simultaneous Measurement of Intraosseous and Cerebrospinal Fluid Pressures in the Lumbar Region; SPINE vol. 10 No. 1 1985.

Bogduk, Nikolai, et al.; Technical Limitations to the efficacy of Radiofrequency Neurotomy for Spinal Pain; NEUROSURGERY vol. 20 No. 4 1987.

Mehta, Mark et al.; The treatment of chronic back pain; Anaesthesia, 1979, vol. 34, pp. 768–775.

Deardorff, Dana L. et al.; Ultrasound applicators with internal cooling for interstitial thermal therapy; SPIE vol. 3594.

Diederich, Chris J. et al.; Ultrasound Catheters for Circumferential Cardiac Ablation; SPIE vol. 3594.

Nau, William H., Ultrasound interstitial thermal therapy (USITT) in the prostate; SPIE vol. 3594.

* cited by examiner

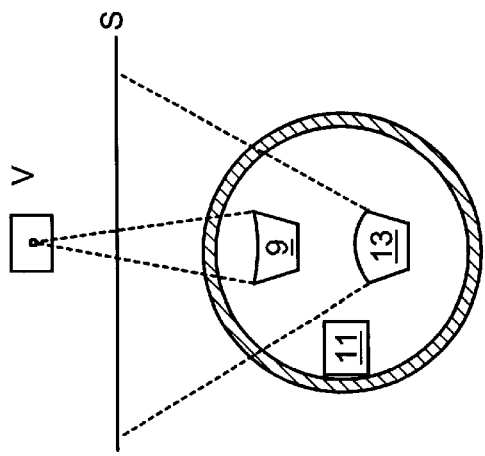
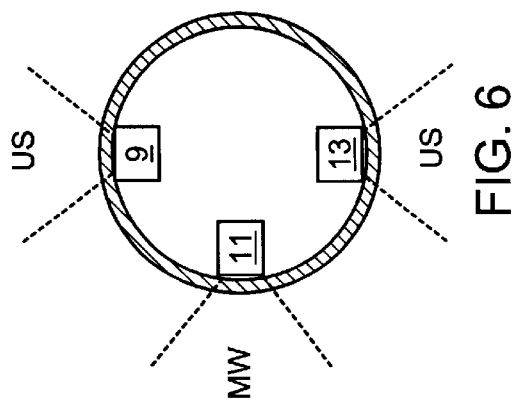
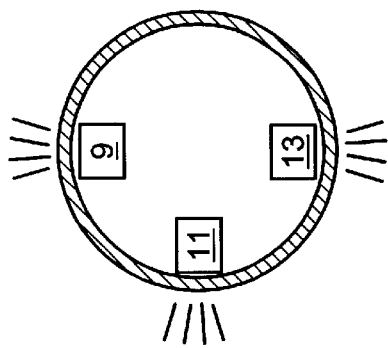
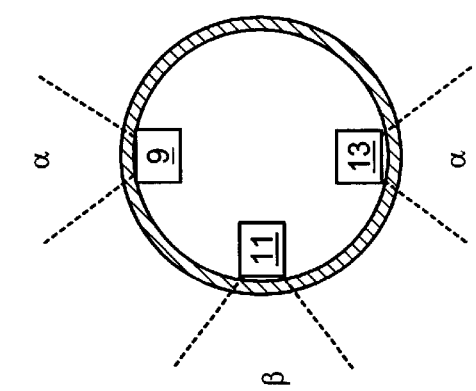
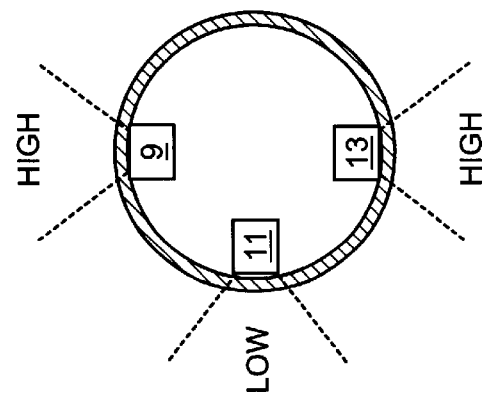

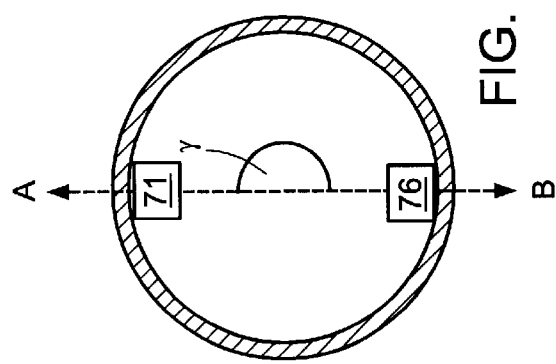
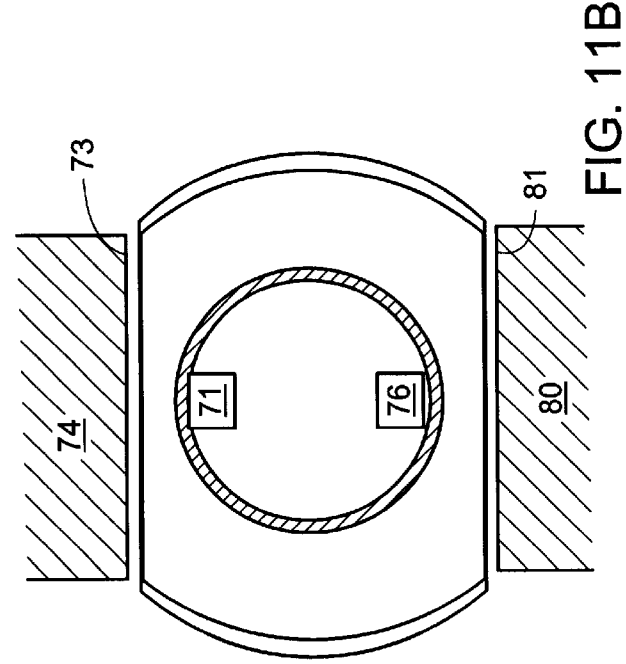
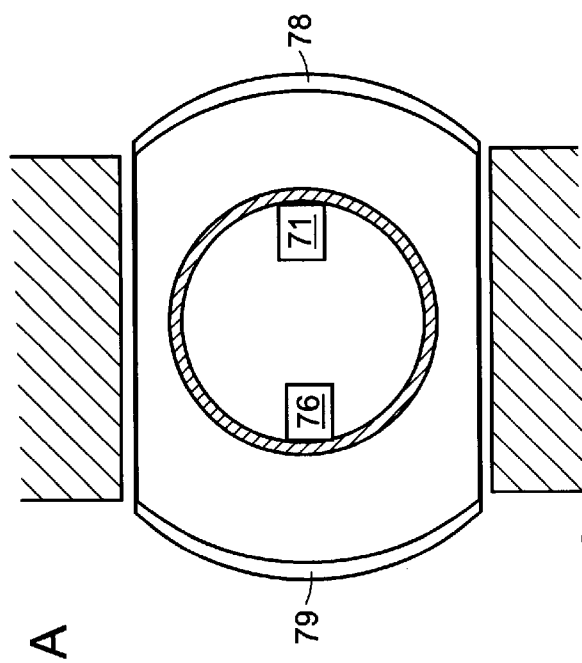
FIG. 11A
FIG. 11B
FIG. 11C

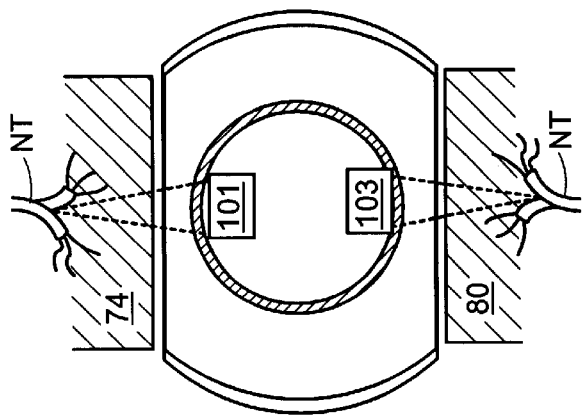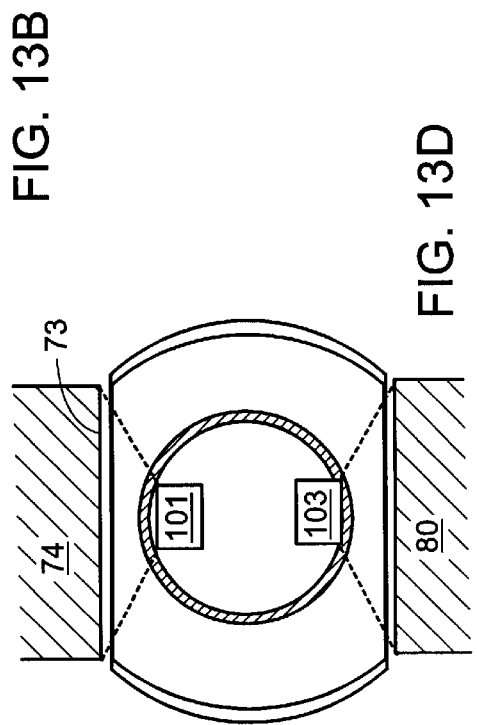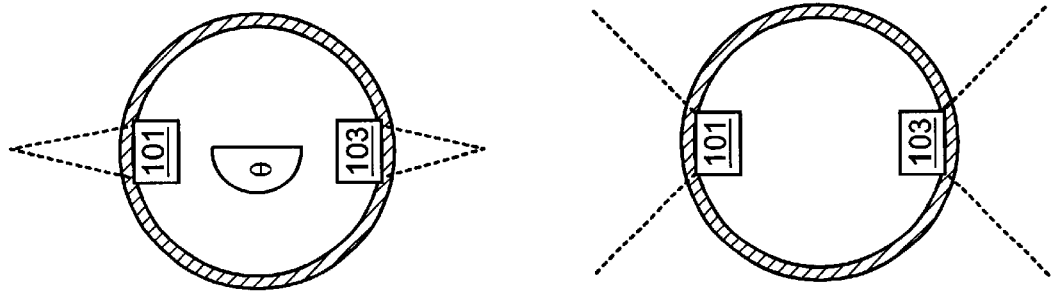

US 6,736,835 B2

EARLY INTERVENTION SPINAL TREATMENT METHODS AND DEVICES FOR USE THEREIN

BACKGROUND OF THE INVENTION

One of the leading causes of spine-related pain is the rupture or degeneration of discs located between lumbar vertebrae ("lumbar intervertebral discs"). Pain in the lower extremities may be caused by compression of spinal nerve roots by such damaged discs, while low back pain may be caused by collapse of these discs and by the adverse effects of bearing weight through a damaged, unstable vertebral joint. One conventional method of managing this problem is to treat the problematic intervertebral disc with energy.

In some instances, the disc is globally heated. U.S. Pat. No. 5,433,739 ("Sluitjer I") proposes inserting an RF electrode or other heating electrode into the intervertebral disc and globally heating the entire intervertebral disc to a temperature significantly above body temperature. See col. 2, lines 52–56. Sluijter I teaches that this process can denervate the neural structures within the disc on a global or semi-global basis, thus relieving the patient of back pain related to stress of the disc and its surface. See col. 5, line 65-col. 6, line 2. Sluijter I further notes that the precise anatomical mechanism of this pain relieving process has not been totally clarified, and discloses not only that anatomical material changes within the disc material itself and the resulting volumetric changes may play some role, but also that the spread of heat to large neural structures in the proximity of the disc may be additional contributory factors of significance. See col. 13, lines 28–37.

In some instances, only the nucleus of the disc is treated. For example, Choy et al., Spine, 17:8 (1992), pp. 949–956, discloses using a laser to evaporate the nucleus pulposus. It is believed that evaporation of the nucleus reduces the pressure within the disc, thereby relieving the pressure upon the nerves therein.

In some instance, only the inner wall of the annulus fibrosus portion of the disc is heated. U.S. Pat. No. 6,261,311 ("Sharkey") proposes using a floppy wand-like probe for fully contacting and resistively heating a portion of the inner wall of the annulus fibrosus to a temperature of about 45–70° C. It is believed that heating the inner wall in this manner may coagulate and/or denervate the collagenous annular wall leading to increased stability of the vertebral joint and/or eliminating the ability of the annular wall to sense pain.

U.S. Pat. No. 6,105,581 ("Eggers") discloses a radiofrequency ("RF") probe which uses an electrically conductive fluid to help ablate tissue within the spine. Eggers discloses coating portions of the probe with an electrically insulative coating to produce "non-active portions of the probe which help the surgeon selectively ablate tissue". See col. 4, line 60 to col. 5, line 10. FIG. 15b of Eggers discloses a transverse cross-section view of a loop electrode wherein active portions of electrode 194 lie in essentially the same plane. Eggers further recites selected spinal applications for this device, including laminectomy/discectomy procedures for treating herniated discs, decompressive laminectomy for stenosis in the lumbosacral and cervical spine, posterior lumbrosacral and cervial spine fusions, treatment of scoliois associated with vertebral disease, foraminotomies to remove the roof of on the intervertebral foramina to relieve nerve root compression and anteror cervical and lumbar discectomies. None of these applications involve the therapeutic treatment of an intervertebral disc which results in an essentially intact disc.

In some instances, the nucleus pulposus is subjected to two power levels of RF energy. For example, U.S. Published patent application No. 2001/0029370 discloses a method of treatment whereby a single probe ablates a portion of the nucleus pulposus as it advances through the nucleus pulposus, and then heats the nucleus pulposus (using bipolar RF energy) as it is withdrawn from the nucleus pulposus in order to coagulate the collagen within the nucleus pulposus.

Some investigators have proposed using ultrasound technology as a means for heating the intervertebral disc. For example, U.S. Pat. No. 5,571,147 ("Sluijter II") proposes using an ultrasound probe to heat the intervertebral disc U.S. Pat. No. 5,620,479 ("Diedrich I") discloses an ultrasound applicator for thermal therapy of tumors and benign tissues using heat generated from acoustic energy, which includes a segmented array of individually controllable tubular ultrasound transducers through which an inner probe extends. See col. 3, lines 6–10. The segmented array disclosed by Diedrich I in FIG. 1 is a linear array of ultrasound sources along the longitudinal axis of the probe. Typically, ultrasound probes are configured to emit ultrasound waves in a fill 360° radius about the axis of the probe. Diedrich I also proposes masking a portion of the radius so that ultrasound is emitted through only a portion of the probe circumference.

U.S. Pat. No. 5,391,197 ("Burdette") proposes radially segmenting the ultra sound transducers (as in FIG. 23a) in order to adjust the power distribution in the angular expanse (see col. 10, line 17).

Some investigators have focused upon nerves contained within the vertebral bodies which are adjacent the problematic disc. For example, PCT Patent Publication No. WO 01/0157655 ("Heggeness") discloses ablating nerves contained within the vertebral body by first boring into the vertebral body with a probe, and then ablating the nerves therein with the probe. Heggeness discloses using laser devices, electricity transmitting devices, fluid transmitting devices and thermal devices, and devices for carrying either chemotherapeutic or radioactive substances as candidate ablation devices.

EPO Patent Published Patent Application No. EP 1 059067 A1 ("Cosman") discloses ablative treatment of metastatic bone tumors, including those within the spine. Pain relief is reportedly achieved by penetrating the bone wall with a suitable probe, and applying heat through the probe to ablate either the bone tumor or the tissue near the bone tumor. Cosman also teaches that the treatment may also be used to ablate the nerves and nerve ramifications in and/or around the bone to desensitize them against further tumor encroachment. See col. 11, lines 7–11.

In general, the prior art methods for treating back pain appear to focus upon identifying a single problematic tissue and treating only that tissue with energy. In addition, the prior art does not disclose or appreciate any need for treating back pain by treating two different tissue sites (e.g., both the intervertebral disc and the adjacent vertebral body portions of the adjacent vertebrae) within the same therapeutic procedure. In addition, the prior art does not disclose or appreciate any need for probes which are adapted for therapeutically treating different tissue sites associated with back pain.

SUMMARY OF THE INVENTION

The present inventors have recognized that back pain may be generated within an individual patient from a multitude of different tissue sites. For example, back pain within a single patient may be generated not only by nerves within that patient's vertebrae, but also by nerves with that patient's intervertebral discs. Simply, there may not be just a single tissue site responsible for a patient's back pain. Accordingly, in one aspect of the present invention, there is provided a method of treating back pain wherein at least two separate tissue sites (e.g., both the intervertebral disc and at least one adjacent vertebra) are therapeutically treated within the same procedure, preferably with a single probe.

In particular, in accordance with the present invention, there is provided a device for therapeutically treating back pain, comprising:
  a) a probe having a proximal portion and a distal portion,
  b) first and second treatment sources, each source located in the distal portion of the probe,
wherein the first treatment source is adapted to therapeutically treat a first tissue site, the second treatment source is adapted to therapeutically treat a second different tissue site, and
wherein the first and second different tissue sites are selected from the group consisting of:
  i) a first intervertebral disc,
  ii) a first vertebra,
  iii) a first spinal ligament, and
  iv) a first spinal facet joint capsule,
  v) a second intervertebral disc,
  vi) a second vertebra,
  vii) a second spinal ligament, and
  viii) a second spinal facet joint capsule.

Also in accordance with the present invention, there is provided a method of treating back pain, comprising the step of therapeutically treating first and second different tissue sites with a single device, each tissue site being selected from the group consisting of:
  i) a first intervertebral disc,
  ii) a first vertebra,
  iii) a first spinal ligament,
  iv) a first spinal facet joint capsule,
  v) a second intervertebral disc,
  vi) a second vertebra,
  vii) a second spinal ligament, and
  viii) a second spinal facet joint capsule.

In addition, the inventors have recognized that back pain may be generated within an individual patient from a multitude of different components within a single spinal tissue site. For example, back pain within a single patient may be generated not only by the nerves within the annulus fibrosus of that patient's intervertebral disc, but also by the nucleus pulposus with that patient's same intervertebral disc. Simply, there may not be just a single component within a tissue site which is responsible for a patient's back pain. Accordingly, in one aspect of the present invention, there is provided a method of treating back pain wherein at least two separate components of the same tissue site (e.g., both the annulus fibrosus and the nucleus pulposus within the same intervertebral disc) are therapeutically treated within the same procedure, preferably with a single probe.

In particular, in accordance with the present invention, there is provided a device for therapeutically treating back pain, comprising:
  a) a probe having a proximal portion and a distal portion,
  b) first and second treatment sources adapted to therapeutically treat an intervertebral disc, each source located in the distal portion of the probe,
wherein the first treatment source is adapted to therapeutically treat a first component of the intervertebral disc, and the second treatment source is adapted to therapeutically treat a second different component of the intervertebral disc.

Also in accordance with the present invention, there is provided a device for therapeutically treating back pain, comprising:
  a) a probe having a proximal portion and a distal portion,
  b) first and second treatment sources adapted to therapeutically treat a vertebra, each source located in the distal portion of the probe,
wherein the first treatment source is adapted to therapeutically treat a first component of the vertebra, and the second treatment source is adapted to therapeutically treat a second different component of the vertebra.

Also in accordance with the present invention, there is provided a device for therapeutically treating back pain, comprising:
  a) a probe having a proximal portion and a distal portion,
  b) first and second treatment sources adapted to therapeutically treat a spinal facet joint capsule, each source located in the distal portion of the probe,
wherein the first treatment source is adapted to therapeutically treat a first component of the spinal facet joint capsule, and the second treatment source is adapted to therapeutically treat a second different component of the spinal facet joint capsule.

Also in accordance with the present invention, there is provided a method of treating back pain, comprising the step of therapeutically treating first and second components within an intervertebral disc with a single device.

Also in accordance with the present invention, there is provided a method of treating back pain, comprising the step of therapeutically treating first and second different components within a vertebra with a single device.

Also in accordance with the present invention, there is provided a method of treating back pain, comprising the step of therapeutically treating first and second different components within a spinal facet joint capsule with a single device.

In one preferred embodiment which treats different tissue sites, the inventors have recognized that back pain may be generated within an individual patient from each of the vertebral bodies which are adjacent a problematic disc. Accordingly, in one aspect of the present invention, there is provided a method of treating back pain wherein at least two separate vertebral bodies (e.g., the vertebral bodies on either side of a problematic disc) are therapeutically treated within the same procedure, preferably with a single probe.

In particular, in accordance with the present invention, there is provided a device for therapeutically treating back pain, comprising:
  a) a probe having a proximal portion and a distal portion,
  b) first and second treatment sources, each source located in the distal portion of the probe,
wherein the first treatment source is adapted to therapeutically treat a first vertebral body, the second treatment source is adapted to therapeutically treat a second vertebral body.

Also in accordance with the present invention, there is provided a method of treating back pain, comprising the step of therapeutically treating first and second vertebral bodies with a single device.

DESCRIPTION OF THE DRAWINGS

FIG. 2 discloses a cross-sectional view of a device of the present invention having sources which emit energy in different directions.

FIG. 3 discloses a cross-sectional view of a device of the present invention having sources which emit energy at different dispersion angles.

FIG. 4 discloses a cross-sectional view of a device of the present invention having sources which emit energy with different intensities.

FIG. 5 discloses a cross-sectional view of a device of the present invention having sources which emit energy with different frequencie.

FIG. 6 discloses a cross-sectional view of a device of the present invention having sources which emit different forms of energy.

FIGS. 11a–11c disclose respectively a cross-section of an embodiment of the present invention having two sources emitting energy in opposite directions, and its operation within a disc.

FIGS. 13a–13d disclose respectively a cross-section of an embodiment of the present invention having two sources, each of whose focal length can be adjusted, and its operation within a disc.

DETAILED DESCRIPTION OF THE INVENTION

Figure 1:
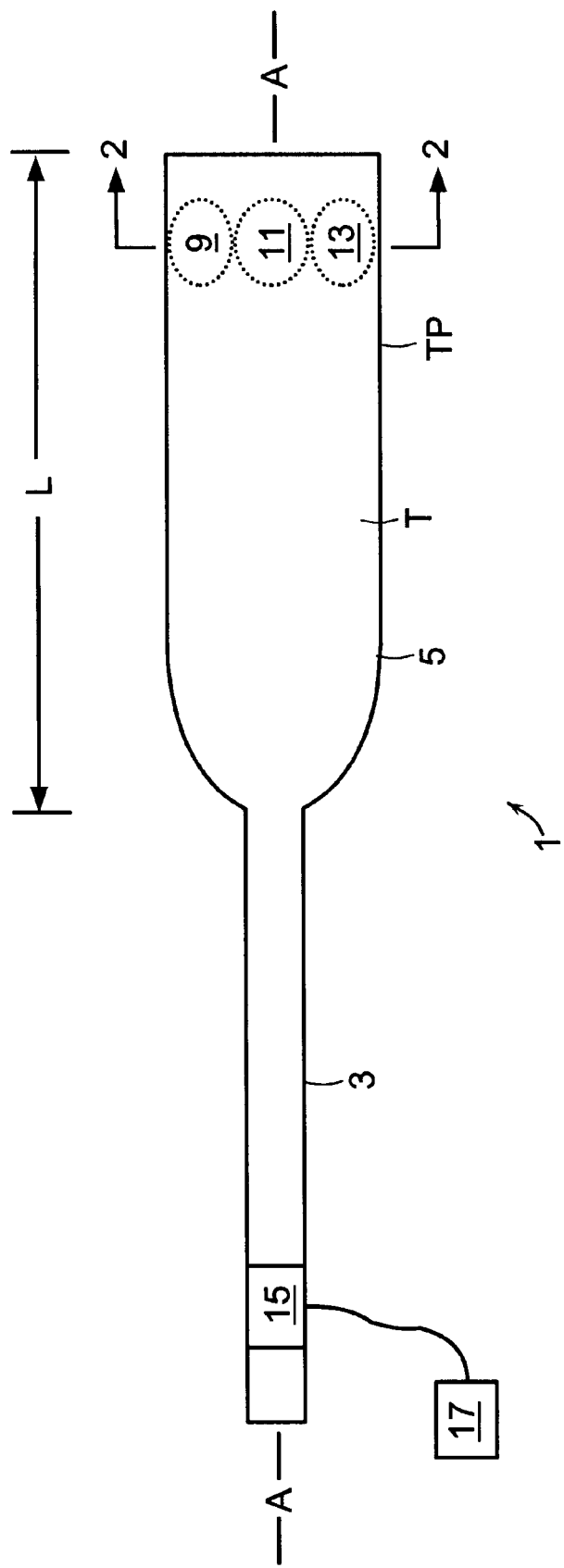
FIG. 1 discloses a side view of an embodiment of a device of the present invention.

For the purposes of the present invention, a "cross-section" of a probe is normal to the longitudinal axis of the probe; and "healthy bone" is bone which is essentially non-tumorous. "Healthy bone" further includes osteoporotic bone, non-osteoporotic bone, fractured bone and intact bone. A nerve which is "denervated" no longer performs its sensing function.

"Different tissue sites" include not only sites having different physiologic structures (e.g., a disc and a vertebra), but also sites having the same physiologic structure which are located in different places (e.g., first and second vertebrae).

"Different components" within a single vertebra include: a) the basivertebral nerve trunk located in the cancellous portion of the vertebral body portion of the vertebra, b) the basivertebral nerve endings located in the endplate portion of the vertebral body portion of the vertebra, and c) the nerve endings located in a facet portion of the vertebra.

"Different components" within a single intervertebral disc include: a) nerve fibrils within the inner portion of the annulus fibrosus, b) collagenous ligaments of the inner portion of the annulus fibrosus, c) the nucleus pulposus, d) nerve fibrils within the outer portion of the annulus fibrosus, e) collagenous ligaments of the outer portion of the annulus fibrosus, "Different components" within a single spinal facet joint capsule include: a) the synovial fluid, b) nerve fibrils within each cartilagenous articular surface, c) nerve fibrils within each capsular ligament, and d) collagenous fibers of each capsular ligament.

In some embodiments, one tissue site selected for therapeutic treatment is the intervertebral disc. Without wishing to be tied to a theory, it is believed that damage to or degeneration of the intervertebral disc may contribute to back or leg pain in at least one of the following ways:

a) innervation of its annulus fibrosus component, leading to chemical and mechanical sensitization of the nociceptors contained therein;
b) mechanical instability due to a fissure in its annulus fibrosus component; and
c) contained herniation of its nucleus pulposus component.

Accordingly, when the intervertebral disc is so selected as the target tissue, the step of therapeutically treating the intervertebral disc may comprise any one of i) coagulating the collagen contained within an annulus fibrosus portion of the disc, ii) denervating the nociceptors contained within an annulus fibrosus portion of the disc, and iii) removing mass from the nucleus pulposus component within the disc, or a combination thereof.

In some embodiments, one tissue site selected for therapeutic treatment is the vertebra, Without wishing to be tied to a theory, it is believed that the vertebra may contribute to back or leg pain in at least one of the following ways:

a) mechanical or chemical sensitization of the basivertebral nerve trunk component located in the cancellous portion of the vertebral body portion of the vertebra;
b) mechanical or chemical sensitization of nerve endings located in the endplate portion of the vertebral body portion of the vertebra; and
c) mechanical or chemical sensitization of nerve endings located in the facet portion of the vertebra.

Accordingly, when the vertebra is selected for therapeutic treatment, the step of therapeutically treating the vertebra comprises denervating at least a portion of the basivertberal nerve trunk located within the cancellous portion of the vertebral body portion of the vertebra, denervating nerves located within the endplate portion of the vertebral body portion of the vertebra, or denervating nerves located within the facet portion of the vertebra.

In some embodiments, one tissue site selected for therapeutic treatment is a spinal ligament selected from the group consisting of a posterior longitudinal ligament ("PLL"), an anterior longitudinal ligament ("ALL") and an interspinous ligament, and preferably is selected from the group consisting of PLL and ALL. Without wishing to be tied to a theory, it is believed that a spinal ligament may contribute to back or leg pain in at least one of the following ways:

a) mechanical or chemical sensitization of nerve fibril component contained within the ligament, or
b) loosening of the ligament, leading to instability.

Accordingly, when a spinal ligament is so selected as the target tissue, the step of therapeutically treating the spinal ligament may comprise any one of i) denervating the nerve fibril component of the spinal ligament, ii) shrinking the loose collagen fiber component of the ligament, or a combination thereof In some embodiments, one tissue site selected for therapeutic treatment is the spinal facet joint capsule. Without wishing to be tied to a theory, it is believed that a spinal facet joint capsule may contribute to back or leg pain in at least one of the following ways:

a) mechanical or chemical sensitization of nerve fibrils contained within the collagenous ligaments of the spinal facet joint capsule,
b) loosening of the collagenous ligaments of the spinal facet joint capsule, or
c) mechanical or chemical sensitization of nerve fibrils contained within the cartilagenous articular surfaces of the spinal facet joint capsule.

Accordingly, when the spinal facet joint capsule is so selected as the target tissue site, the step of therapeutically treating the spinal facet joint capsule may comprise either i) denervating the nerve fibrils within the ligament portion of the spinal facet joint capsule, ii) shrinking the loose collagen fiber portion of the ligament portion of the spinal facet joint capsule, or iii) denervating the nerve fibrils contained within the cartilagenous articular surfaces of the spinal facet joint capsule.

In particularly preferred embodiments, the first tissue site is an intervertebral disc and the second tissue site is a vertebra. When these tissue sites are so selected, the step of therapeutically treating may comprise heating the annulus fibrosus portion of the disc and denervating at least a portion of the nerves in the vertebra. In some embodiments, this method further comprises the step of b) removing at least a portion of the nucleus pulposus of the disc. The step of removing at least a portion of the nucleus pulposus may include the step of liquifying the nucleus pulposus.

In some preferred embodiments, the first tissue site is an intervertebral disc and the second tissue site is a spinal ligament. Preferably, the spinal ligament is selected from the group consisting of PLL and ALL.

In some embodiments, the first tissue site is a vertebra and the second tissue site is a spinal ligament. Preferably, the spinal ligament is selected from the group consisting of PLL and ALL.

Although in some instances, a surgeon may choose to practice the present invention by therapeutically treating two different tissue sites, in other embodiments, the surgeon may choose to practice the present invention by therapeutically treating two different components of the same tissue site.

For example, in disc-related embodiments, the first treatment source is adapted to therapeutically treat a first component of the intervertebral disc, and the second treatment source is adapted to therapeutically treat at least a second different component of the same intervertebral disc. In some embodiments thereof, the first treatment source is adapted to therapeutically treat at least a portion of an annulus fibrosus within an intervertebral disc, and the second treatment source is adapted to therapeutically treat at least a portion of a nucleus pulposus within the intervertebral disc. In other embodiments, the first treatment source is adapted to therapeutically treat at least an interior component of the intervertebral disc (such as the nucleus pulposus or the inner wall of the annulus fibrosus), and the second treatment source is adapted to therapeutically treat an exterior component of the intervertebral disc (such as the outer wall of the annulus fibrosus).

In some embodiments wherein the vertebral body portion of the vertebra is treated, the first treatment source is adapted to therapeutically treat a first component of the vertebral body, and the second treatment source is adapted to therapeutically treat at least a second different component of the same vertebral body. In some embodiments thereof, the first treatment source is adapted to therapeutically treat at least a portion of the basivertebral nerve trunk located in the cancellous bone portion of the vertebral body, and the second treatment source is adapted to therapeutically treat a nerve ending located in the endplate portion of the vertebral body.

In ligament-related embodiments, the first treatment source is adapted to therapeutically treat a first component of the ligament, and the second treatment source is adapted to therapeutically treat at least a second different component of the same ligament. In some embodiments thereof, the first treatment source is adapted to therapeutically treat a nerve fibril of the spinal ligament, and the second treatment source is adapted to therapeutically shrink the loose collagen fiber component of the ligament.

In facet joint-related embodiments, the first treatment source is adapted to therapeutically treat a first component of the spinal facet joint capsule, and the second treatment source is adapted to therapeutically treat at least a second different component of the same spinal facet joint capsule. In some embodiments thereof, the first treatment source is adapted to therapeutically treat a nerve fibril contained within the ligamentous portion of the spinal facet joint capsule, and the second treatment source is adapted to therapeutically treat nerves in the cartilagenous articular surfaces in the capsule. In other embodiments thereof, the first treatment source is adapted to therapeutically treat the collagen fiber portion of the ligaments in the capsule, and the second treatment source is adapted to therapeutically treat the nerves in the cartilagenous articular surfaces.

In general, the device should have a shape which causes minimal disruption to the patient's internal anatomy. It should be made of or coated with biocompatible materials such as polyimide. Since the device will enter the human body, it should be sterile.

Now referring to FIG. 1, preferably, the device is shaped for insertion into and withdrawl from the human body. As such, the device typically comprises a probe 1 having a shape suitable for entry into and withdrawl from the body. The probe may comprise a proximal portion 3 and a distal portion 5. The proximal portion of the probe may include a power lead 15 for activating the treatment sources. Typically, distal portion 5 comprises i) a tubular portion T having a tube perimeter TP and ii) a plurality of treatment sources (such as sources 9, 11 and 13) located on or within the tube T. The function of tubular portion T is to essentially transport the treatment sources, and it can be solid or hollow.

Together, the proximal and distal portions of the probe may define a longitudinal axis A and a cross-section CS, as shown in FIG. 1. In many embodiments, the distal portion of the probe has length L (measured along axis A) and a cross-section CS whereby the length L of the distal portion is at least 10 times longer than the cross-section CS of the distal portion, preferably at least 100 times longer.

In some embodiments, the probe is shaped for insertion into an intervertebral disc. As such, it has a shape suitable for forming a bore in the disc for both entry into and withdrawl from the intervertebral disc. Preferably, the cross section of the distal portion of the device is less than the height of the targeted disc.

In some embodiments, the probe is shaped for insertion into a vertebral body portion of the vertebra. As such, it has a shape suitable for forming a bore in the vertebral body, and for entry into and withdrawl from the vertebral body.

In some embodiments, the probe is shaped for insertion between two vertebral bodies, but outside the intervertebral disc.

In selected embodiments, the two treatment sources provided within the same probe may therapeutically act upon i) different tissue sites, or ii) different components of the same tissue site by embodiments including but not limited to the embodiments disclosed in the following:

Now referring to FIG. 2, in some embodiments, a treatment source may be radially biased so as to emit energy in a preferred radial direction. For example, source 9 may emit energy preferentially in the 12 o'clock direction while source 13 may emit energy preferentially in the 6 o'clock direction. Providing a source with a preferred radial emission direction may be accomplished, for example, by masking a portion of the circumference of a cylindrical source (see Deardorf, Ultrasound applicators with internal cooling for interstitial thermal therapy, SPIE Conference of Thermal Treatment of Tissue with Image Guidance, January 1999), or by using segmented emission sources, as in FIG. 19B of Burdette, the specification of which is incorporated by reference. When the source is designed so as to produce an elliptical energy pattern, the emission pattern is considered to be bi-directional along the longitudinal axis of the ellipse.

Now referring to FIG. 3, in some embodiments, the sources may emit energy in different dispersion angles. For example, source 9 may have a concave surface so that energy emitted therefrom focuses upon relatively small volume V, while source 13 may have a convex surface so that energy emitted therefrom can couple with a broad surface S.

Now referring to FIG. 4, in some embodiments, the sources may emit energy with different intensities. For example, sources 9 and 13 may provide a high intensity emission H while source 11 may provide a low intensity emission L.

Now referring to FIG. 5, in some embodiments, the sources may emit energy with different frequencies. For example, sources 9 and 13 may have a high frequency α emission while source 11 may have a low frequency β emission.

Now referring to FIG. 6, in some embodiments, the sources may emit different types of energy. For example, source 9 may emit ultrasound energy (US) while source 11 may emit microwave energy (MW).

The treatment source of the present invention includes all forms of energy which may have a therapeutic effect. Such sources include but are not limited to energy output devices (such as electrical sources, light sources, and acoustic sources) and chemical delivery sources.

Examples of electrical sources include a) sources which produce resistive heating, and b) radiofrequency sources. Examples of therapeutic devices having sources which produce resisitive heating can be found in U.S. Pat. No. 6,261,311, the specification of which is incorporated by reference. When radiofrequency sources are used, either monopolar or bipolar sources may be employed. Preferably, the radiofrequency source is bipolar. Examples of therapeutic devices having radiofrequency sources can be found in U.S. Pat. Nos. 6,105,581 and 5,458,596, the specification of which is incorporated by reference.

Examples of light sources include UV sources, visible light sources, and diffused laser light sources. Preferably, the light source provides interstitial penetration of the target tissue to achieve a desired depth of penetration. Examples of therapeutic devices having light sources can be found in U.S. Pat. Nos. 5,437,661 and 5,084,043, the specifications of which are incorporated by reference.

Examples of acoustic sources include ultrasonic transducers. Examples of therapeutic devices having ultrasonic transducers can be found in U.S. Pat. No. 5,620,479 ("Diedrich I") and U.S. Pat. No. 5,733,315 ("Lax"), the specifications of which are incorporated by reference.

Examples of chemical delivery sources include a pair of chemicals which when combined produce an exothermic reaction. In one embodiment, the chemical sources comprises a monomer and a chemical which, when combined with the monomer, produces an exothermic cross-linking reaction to produce a polymer.

In some embodiments, the first treatment source provides therapy by a form of energy which is different than that of the second treatment source. For example, the first treatment source may be an ultrasonic transducer and the second treatment source may be a resistive heating element. In another example, the first treatment source may be an ultrasonic transducer and the second treatment source may be a microwave heating source. In another example, the first treatment source may be an ultrasonic transducer and the second treatment source may be an RF heating source, preferably a bipolar RF source. In another example, the first treatment source may be an energy source (such as an ultrasonic transducer) and the second treatment source may be chemical delivery source (preferably a source which delivers a pair of chemicals which when combined have an exothermic reaction).

In some embodiments, at least one of the treatment sources comprises an ultrasound transducer. One advantage of ultrasonic transducers is the ability to focus the ultrasound energy upon a small volume of tissue far away from the transducer. Accordingly, a device having an ultrasound transducer may be inserted either a) into the intervertebral disc or b) between two adjacent vertebrae but outside the disc, and the ultrasound energy from this transducer may be focused in such a way as to heat the adjacent vertebrae, a spinal facet joint capsule, or a portion of the adjacent PLL or ALL spinal ligament. At the same time, the second treatment source (which also may be ultrasound or may be another type of treatment source such as a resistive heating element) may be used to heat the annulus fibrousus portion of the disc or to coagulate or liquify the collagen component of the nucleus pulposus therein.

In many embodments, the ultrasound transducer comprises a ceramic component, and typically is a sintered, polycrystalline ceramic component. In some embodiments using two ultrasound transducers to heat different tissue sites, the ceramic component of the first ultrasonic transducer has a composition which is different than the ceramic component of the second ultrasonic transducer. The different ceramic component compositions can produce different frequencies of ultrasound given the same energy input. The different frequencies will in turn couple selectively to different tissue structures. This difference in frequencies produces a different acoustic penetration of ultrasound, and the surgeon can exploit this difference by using a particular transducer type to treat a particular tissue site. For example, if the surgeon desires to treat a first soft tissue structure (such as an intervertebral disc or a spinal ligament), the surgeon would select a ceramic component which produces a relatively high frequency. Conversely, if the surgeon desires to treat a second hard tissue structure (such as a vertebral body), the surgeon would select a ceramic component which produces a relatively low frequency.

In some embodiments using two ultrasound transducers to heat different tissue structures, the wall thickness of the first ultrasonic transducer ceramic component is different than the wall thickness of the second ultrasonic transducer ceramic component. This difference produces different frequencies of ultrasound given the same energy input, and the surgeon can exploit this difference by using a particular transducer to advantageously couple a particular frequency with a particular tissue site. For example, if the surgeon desires to treat a first soft tissue structure, the surgeon would desire a relatively high frequency and so would select a ceramic component having a relatively thin wall thickness. Likewise, if the surgeon desires to treat a second hard tissue structure, the surgeon would select a ceramic component having a relatively thick wall thickness. In some embodiments, the wall thickness of the first ceramic component is at least 20% thicker (and in some embodiments at least 50% thicker) than the wall thickness of the second ceramic component.

In many embodiments, the ceramic component of the ultrasound transducer has a coating thereon. These coatings are typically made of a material selected from the group consisting of a metal (such as gold) or a polymer. These coatings may be employed to alter the properties of the ultrasound wave emitted from the ceramic component. They are typically acoustically absorbent. However, the coating may also be used to modify other acoustic outputs. For example, the coating may change the dispersion pattern of the ultrasound emission (by, for example, masking), change its frequency, or change its focus. Therefore, in some embodiments using two ultrasound transducers to heat different tissue structures, each transducer has a coating, and the coating upon the first ultrasonic transducer ceramic component is different than the coating upon the second ultrasonic transducer ceramic component. In other embodiments using two ultrasound transducers to heat different tissue structures, only one transducer has a coating. In some embodiments using two ultrasound transducers to heat different tissue structures, each transducer has a coating, and the coating upon the first ultrasonic transducer ceramic component is the same as the coating upon the second ultrasonic transducer ceramic component.

In some embodiments, at least one of the treatment sources comprises a resistive heating element. A resistive heating element provides the advantage of being able to heat by surface conduction. Accordingly, a resistive heating element is most advantageous when the surgeon is seeking to heat a surface, such as the internal wall of the annulus fibrosus portion of the disc or the external wall of the annulus fibrosus.

In some embodiments, at least one of the treatment sources comprises a radiofrequency heating element. A radiofrequency heating element provides the advantage of being able to heat or ablate. Accordingly, a radiofrequency heating element is most advantageous when the surgeon is seeking to ablate a tissue.

Preferably, the radiofrequency heating element is bipolar. A bipolar RF element provides the advantage of being able to localize current flow, and thereby ablate without producing substantially high temperatures in the surrounding tissues. Accordingly, a radiofrequency heating element is most advantageous when the surgeon is seeking to ablate a particular tissue without disturbing nearby tissues.

In some embodiments wherein ablation of a portion of the basivertebral nerve is desired, an RF element is desirably selected.

In some embodiments, a single treatment source is dynamically controllable (e.g., its particular output can be changed during a procedure). When the source is an ultrasonic transducer, the acoustic output may be dynamically controlled by changing the power intensity, the frequency, the angle of dispersion, the focus, or other dynamically controllable parameters. In some embodiments using ultrasound, the device may further comprise a feedback monitor which monitors the changes in the acoustic properties of the treated tissue, and provides feedback to the device which then directs an adjustment of the ultrasound emission. In some embodiments using RF, the device may further comprise a feedback monitor which monitors the changes in the impedence of the treated tissue, and provides feedback to the device which directs an adjustment of the RF emission.

In some embodiments, different treatment sources are individually controllable (e.g., a first source has a different output than a second source). When the source is an ultrasonic transducer, the acoustic output may be controlled by intensity, by frequency, by angle of dispersion, by focus, or by other controllable parameters, such as inputs. For example, the device may comprise two different channel boxes which drive respective sources at different frequencies.

In this way, the intensity and quality of the acoustic output may be tailored for the particular application. For example, in some embodiments, now referring to FIG. 7a, each of treatment sources 71 and 72 (which are preferably ultrasound transducers) preferentially emit energy in respective first A and second B directions defining an angle θ of about 90 degrees therebetween. When this device is placed into an intervertebral disc (as in FIG. 7b), transducer 71 faces the upper endplate 73 of vertebral body 74 while transducer 72 faces the collagenous annulus fibrosus 75 (preferably the posterior inner wall thereof). Because bone couples much more efficiently with ultrasound than with collagen, endplate 73 will heat up much more quickly than the annulus fibrosus 75. Accordingly, controlling the output of bone-directed transducer 71 so that it produces less ultrasound energy than the collagen-directed transducer 72 will allow the surgeon to provide enough energy to both the bone and annulus fibrosus so that each tissue heats up to its desired temperature in about the same time. This ability to produce such a tailored results provides an advantage over conventional devices.

Therefore, in some embodiments, the first transducer is adapted to heat the endplate while the second transducer is adapted to heat the annulus fibrosus, and the energy flux from the first transducer is less than that of the second transducer.

Figure 7A:
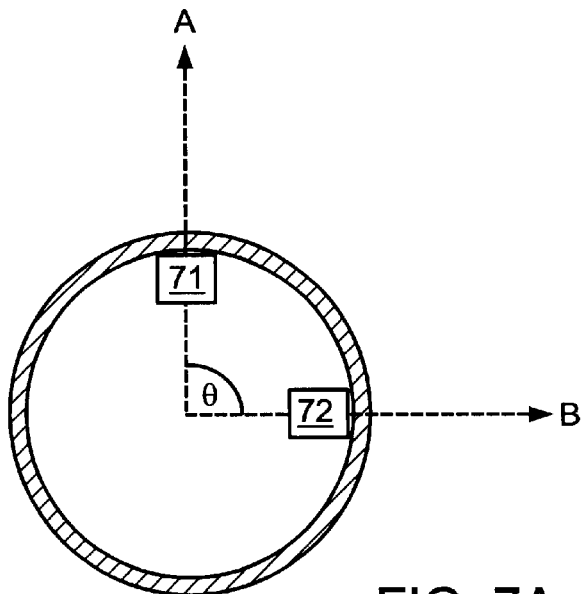
FIGS. 7a and 7b disclose respectively a cross-section of an embodiment of the present invention whose sources emit energy in directions which form a 90 degree angle, and its operation within a disc.
Figure 7B:
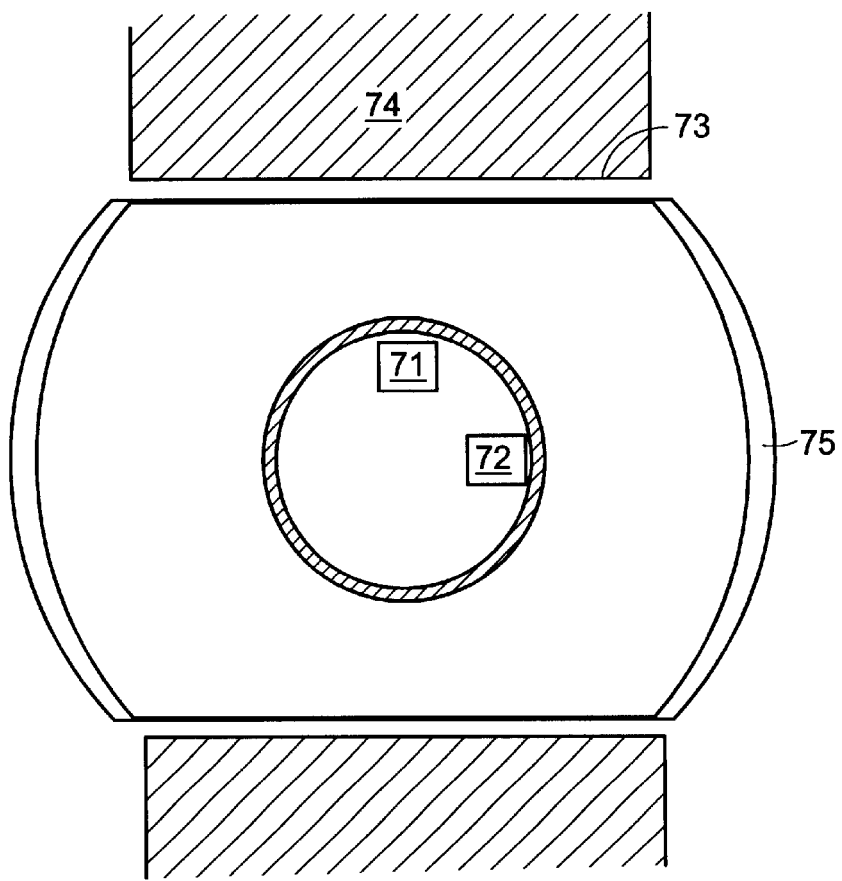
Figure 8A:
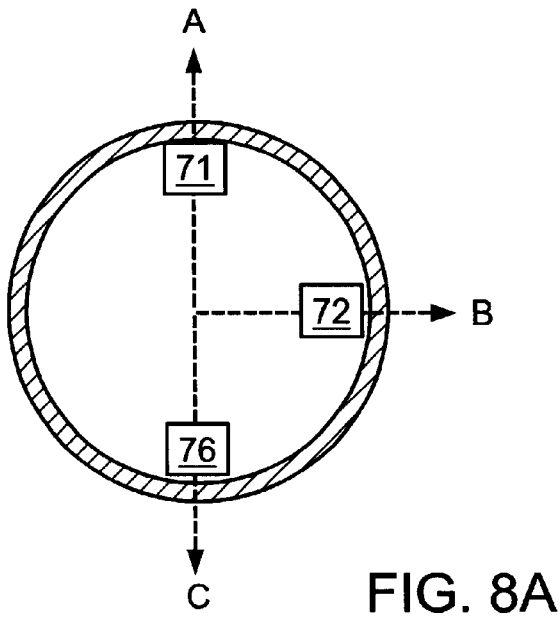
FIGS. 8a and 8b disclose respectively a cross-section of an embodiment of the present invention having three sources, and its operation within a disc.
Figure 8B:
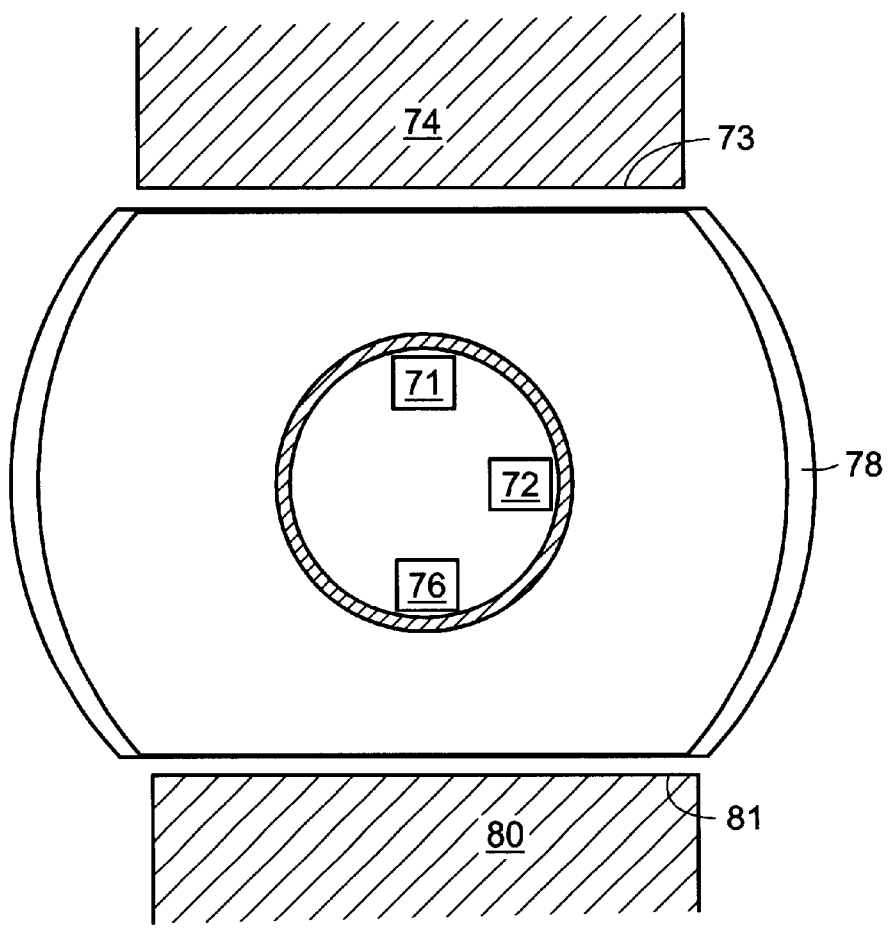

Now referring to FIG. 8a, in some embodiments, transducer 76 which emits energy substantially in the C direction is added to the device of FIG. 7a directly opposite from transducer 71 so that both the upper 73 and lower 81 endplates can be heated at the same time (as in FIG. 8b).

Figure 9A:
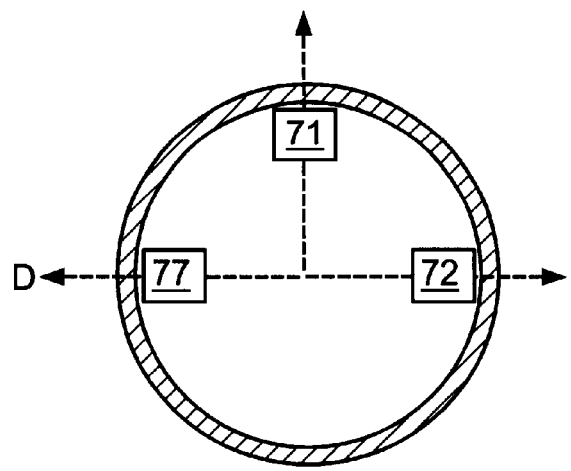
FIGS. 9a and 9b disclose respectively a cross-section of an embodiment of the present invention having three sources, and its operation within a disc.
Figure 9B:
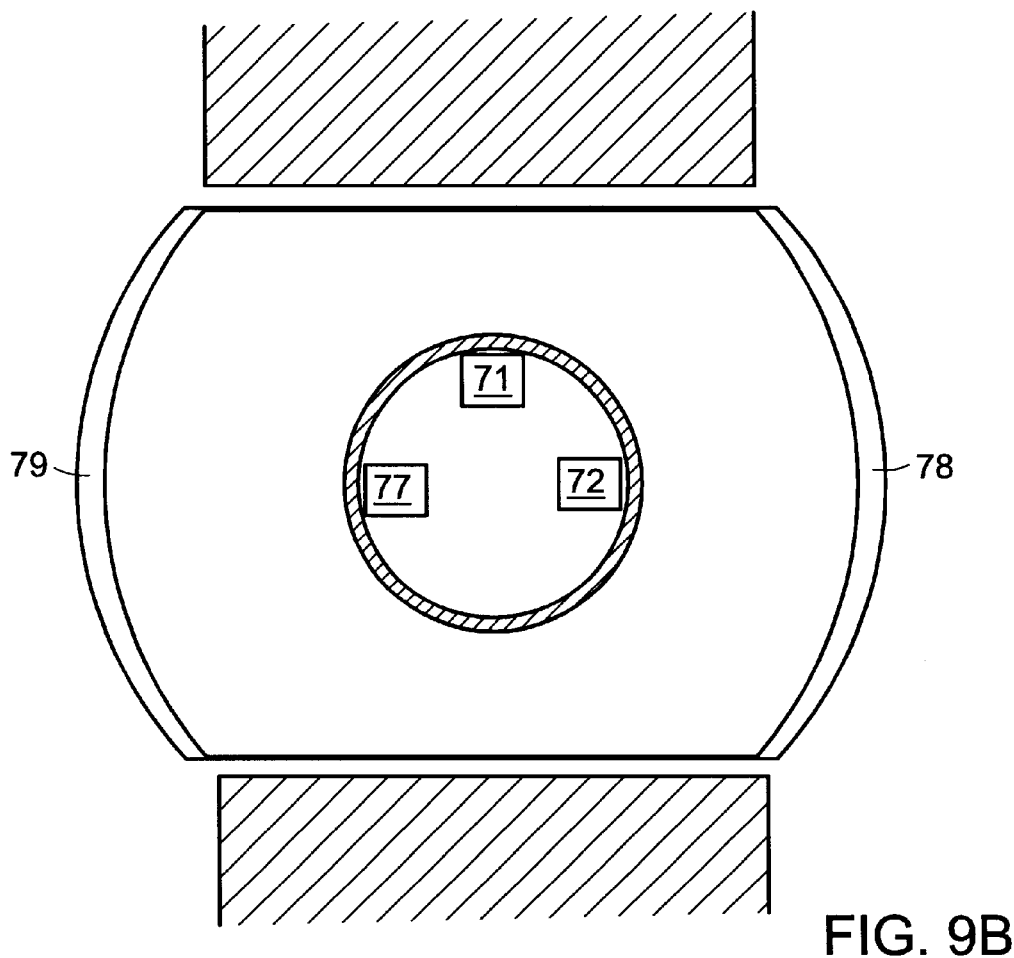

Now referring to FIG. 9a, in some embodiments, transducer 77 which emits energy substantially in the D direction is added to the device of FIG. 7a so that both the posterior 78 and anterior 79 walls of the annulus fibrosus can be heated at the same time (as in FIG. 9b).

Figure 10A:
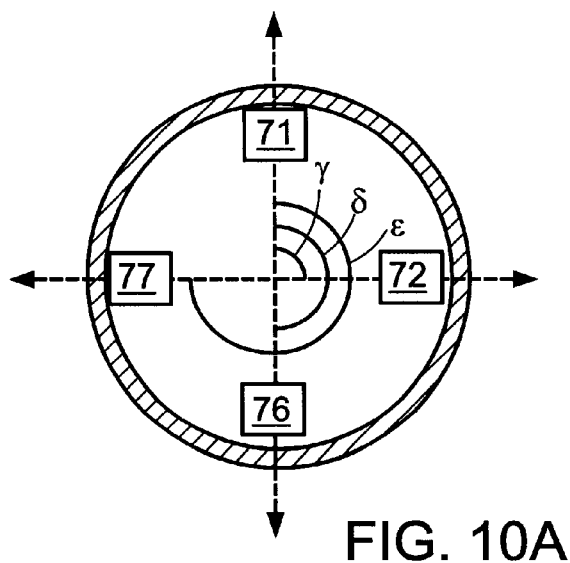
FIGS. 10a and 10b disclose respectively a cross-section of an embodiment of the present invention having four sources, and its operation within a disc.
Figure 10B:
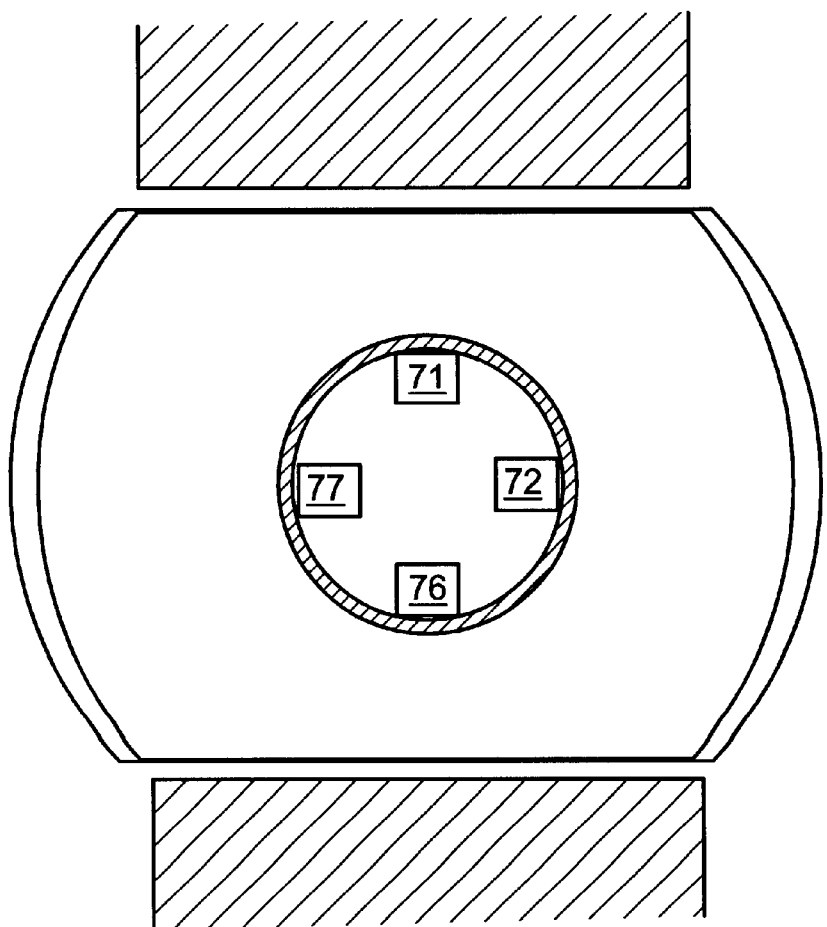

Now referring to FIG. 10a, in some embodiments, both treatment sources 76 and 77 (which are preferably both ultrasound transducers) are added to the device of FIG. 7a so that both endplates and both the posterior and anterior walls of the annulus fibrosus can be heated at the same time (as in FIG. 10b). When the device comprises at least four treatment sources (preferably at least two and more preferably all four being ultrasound sources), the device can simultaneously treat upper and lower vertebral bodies and posterior and anterior portions of the annulus fibrosis from a location within the intervertebral disc. Preferably, the first, second, third and fourth sources emit energy in first, second, third and fourth directions, the directions respectively defining angles $\gamma$, $\delta$ and $\epsilon$ therebetween, wherein angle $\gamma$ is between 80 and 100 degrees, angle $\delta$ is between 170 and 190 degrees, angle $\epsilon$ is between 260 and 280 degrees.

In another instance which demonstrates the advantage of having individually controllable sources, now referring to FIG. 11a, each of treatment sources 71 and 76 are preferably ultrasound transducers which emit energy substantially in the respective first A and second B directions defining an angle $\theta$ of about 180 degrees therebetween. When this device is placed into the intervertebral disc as shown in the FIG. 11b, transducer 71 faces the endplate 73 of upper vertebral body 74 while transducer 76 faces the endplate 81 of lower vertebral body 80. In this instance, the surgeon can first simultaneously treat sources of pain in the opposing vertebral bodies by using a first power level which will effectively therapeutically treat the vertebral bodies. Then, the surgeon can rotate the device 90° so that transducers 71 and 76 now face the opposing wall portions 78 and 79 of the annulus fibrosus (as in FIG. 11c). The surgeon can then treat sources of pain in the annulus fibrosus by using a second power level which will effectively heat the walls of the annulus fibrosus. The second power level may be sufficient to coagulate collagen within the walls, or may be sufficient to denervate the nerves within the walls. This ability to produce such a tailored results provides an advantage over conventional devices.

In some embodiments, the treatment steps are reversed whereby the annulus fibrosus is first treated, and then the vertebral bodies are then treated.

Figure 12C:
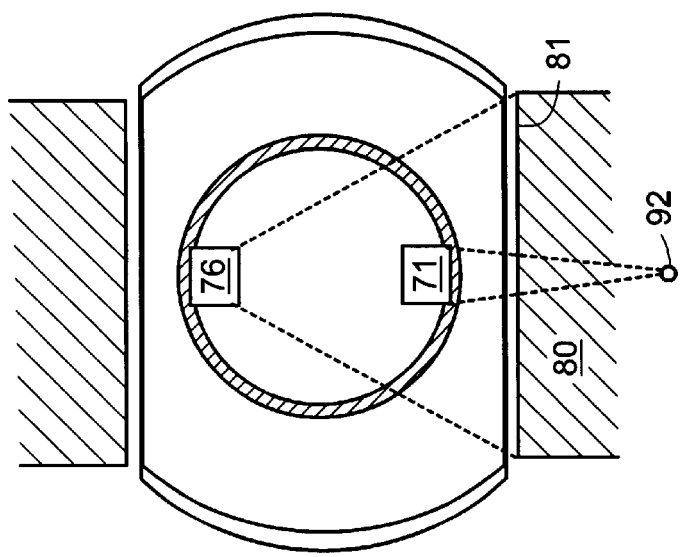
FIGS. 12a–12c disclose respectively a cross-section of an embodiment of the present invention having one concave and one convex source emitting energy in the same direction, and its operation within a disc.
Figure 12A:
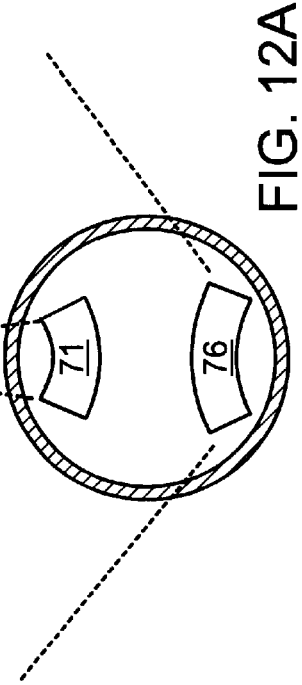
Figure 12B:
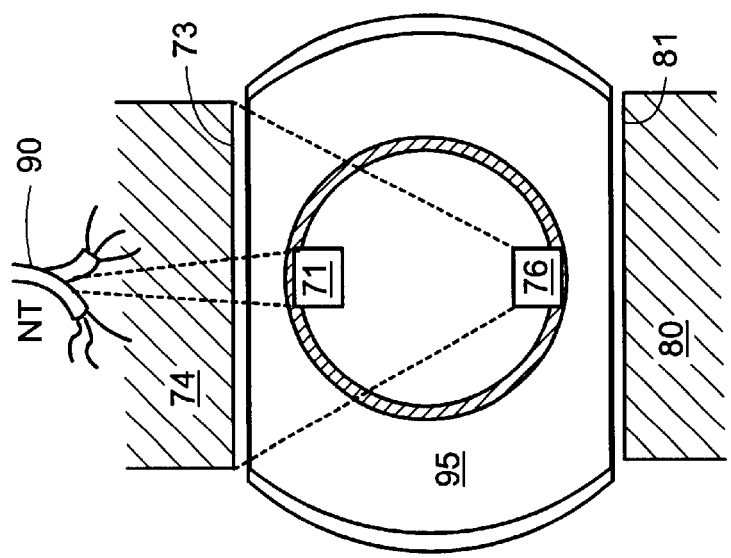

In another instance which demonstrates the advantage of having individually focused sources, now referring to FIG. 12a, each of treatment sources 71 and 76 are preferably ultrasound transducers which emit energy in substantially the same direction. Whereas treatment source 71 is concave and produces a focused energy pattern within volume V, treatment source 76 is convex and produces a dispersed energy pattern. When the device of FIG. 12a is placed into the intervertebral disc as shown in the FIG. 12b, each transducer 71 and 76 faces upper vertebral body 74. However, whereas upper transducer 71 is focused to treat sources of pain deep within the upper vertebral body (such as nerve trunk NT), lower transducer 76 focuses its energy upon the vertebral endplate 73 (to treat the nerve endings located therein). In use, activation of source 76 will cause a temperature rise within the endplate sufficient to denervate the plurality of nerve endings located in or near the endplate, while activation of source 71 will cause a temperature rise in the vicinity of nerve trunk NT sufficient to denervate the basivertebral nerve substantially at its source.

After so treating the upper vertebral body, the surgeon may then flip the probe 180 degrees (as in FIG. 12c), in order to similarly treat the lower vertebral body.

Figure 12D:
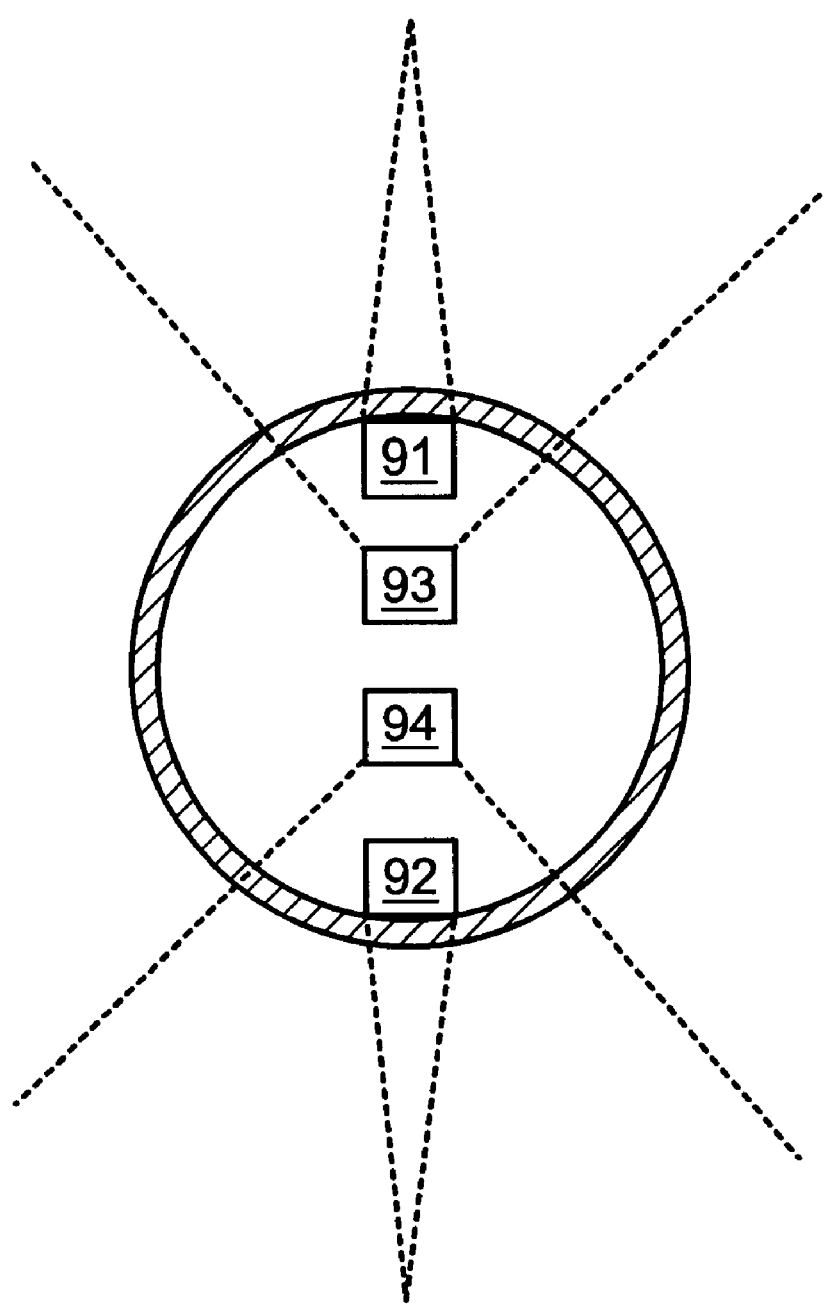
FIG. 12d discloses a cross-section of an embodiment of the present invention having two concave and two convex sources, and its operation within a disc.

Now referring to FIG. 12d, in another embodiment, two concave sources 91, 92 and two convex sources 93, 94 are disposed within the probe so that simultaneous treatment of both the endplates and the nerve trunks may occur. In particular, the concave sources can heat the respective nerve trunks while the convex sources heat the vertebral endplates.

In some instances, the temperature rise within an endplate treated with the device of FIG. 12a may also be sufficient to cause heat to radiate from the vertebral endplate to the intervertebral disc 95 in an amount sufficient to cause at least one of collagen shrinkage or nerve denervation within the intervertebral disc.

In another instance which demonstrates the advantage of having individually controllable sources, now referring to FIG. 13a, each of treatment sources 101 and 103 emit energy in first and second directions defining an angle $\theta$ of about 180 degrees therebetween. When this device is placed into the intervertebral disc as shown in the FIGS. 13b and 13d, source 101 faces the endplate 73 of upper vertebral body 74, while source 103 faces the endplate 81 of lower vertebral body 80. Now referring to FIG. 13b, the surgeon can first treat sources of pain deep within the vertebral bodies (such as nerve trunks NT) by using a first focus which will effectively direct substantially all the energy to the nerve root. Now referring to FIG. 13c, the surgeon can adjust the foci of the sources in situ to a second broader focus. Now referring to FIG. 13d, the surgeon can then focus all the energy upon the vertebral endplates 73 and 81, thereby heating up each endplate to a desired temperature.

The sequence steps of this embodiment may also be reversed.

In some embodiments, the probe may have a single in-situ focus adjustable source, thereby requiring the probe to be flipped as described above in order to treat each adjacent vertebral body.

In some instances, the temperature rise within the endplate will be sufficient to denervate the plurality of nerve endings located in or near the endplate. In some instances, the temperature rise within the endplate will be sufficient to cause heat transfer from the vertebral endplate to the intervertebral disc in an amount sufficient to cause at least one of collagen shrinkage or nerve denervation within the intervertebral disc.

This ability to produce such a tailored results provides an advantage over conventional devices.

Figure 14A:
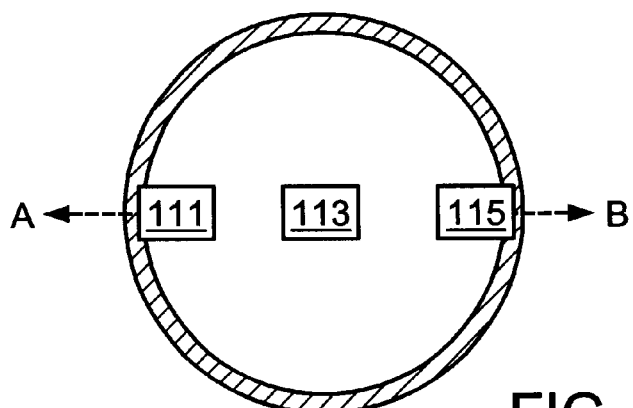
FIGS. 14a–14b disclose respectively a cross-section of an embodiment of the present invention having two lateral sources and one intermediate source, and its operation within a disc.
Figure 14B:
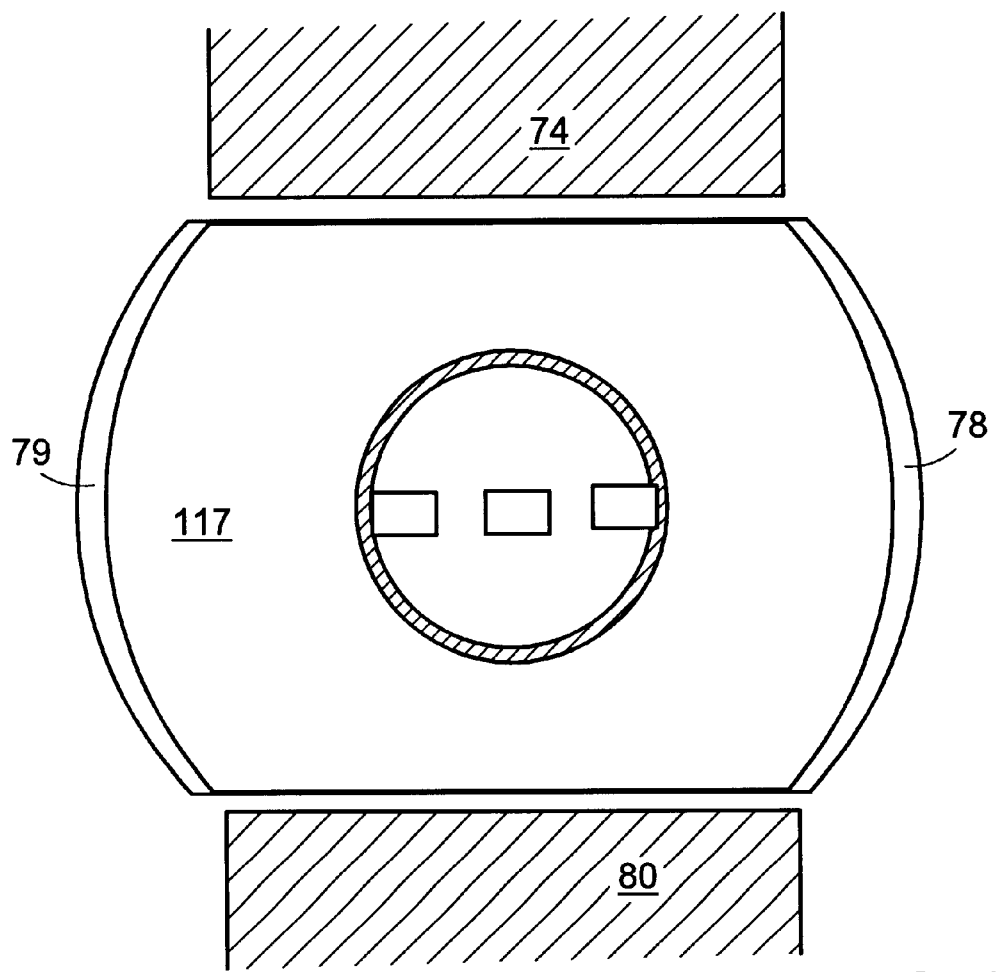

In another instance which demonstrates the advantage of having individually controllable sources, now referring to FIG. 14a, lateral treatment sources 111 and 115 are ultrasound transducers which emit energy in first A and second B directions defining an angle of about 180 degrees therebetween. On the other hand, middle local treatment source 113 is a source for more localized heating, such as a resistive heating element, a bipolar RF heating element, or a concave ultrasound transducer having a short focus. When this device is placed into the nucleus pulposus of an intervertebral disc as shown in FIG. 14b, transducer 115 faces the right portion of the disc's annulus fibrosus portion 78, while transducer 111 faces the left portion of the disc's annulus fibrosus portion 79. In one embodiment, the surgeon can first depressurize the nucleus pulposus by activating the local source 113 which will effectively locally deposit all of its energy into the nucleus pulposus and vaporize at least a portion of it. Next, the surgeon can activate the lateral ultrasound transducers to deposit their energy upon the respective lateral walls of the annulus fibrosus 78 and 79, thereby heating up these walls to a desired temperature. In some instances, the temperature rise within the walls will be sufficient to denervate the plurality of nerve endings located in or near the walls. In some instances, the temperature rise within the walls will be sufficient to cause collagen shrinkage within the walls.

Alternatively, the sequence of treatment steps in this procedure may be reversed, wherein the surgeon first treats the annulus fibrous and then treats the nucleus pulposus.

Alternatively, the surgeon can activate all of the sources at the same time.

This ability to produce such a tailored results provides an advantage over conventional devices.

In some embodiments wherein the first and second treatment sources are of the same type (e.g., both are ultrasonic transducers), the surface energy flux of the first source may be different than the surface energy flux of the second source. In preferred embodiments, the surface energy flux of the first source is at least twice as large as the surface energy flux of the second source. This embodiment would have find advantageous in simultaneously treating two different tissues types (e.g., the vertebra and the annulus fibrosus of the intervertebral disc) which couple to ultrasound differently.

Similarly, in some embodiments wherein the first and second treatment sources are of the same type (e.g., both are ultrasonic transducers), the surface energy flux density of the first source may be different than the surface energy flux density of the second source. In preferred embodiments, the surface enery flux density of the first source is at least twice as large as the surface energy flux density of the second source.

Now referring to FIG. 7a, in some embodiments, first 71 and second 72 treatment sources emit energy in first and second directions defining an angle θ of between 45 and 135 degrees, preferably between 60 and 120 degrees, more preferably between 80 and 100 degrees, most preferably about 90 degrees. In this most preferred embodiment, the emissions from the sources are substantially orthogonal. Such a device would be useful for simultaneously treating both a vertebral body and a wall of the annulus fibrosus from the middle of the intervertebral disc, or from between adjacent vertebrae but outside the disc.

Now referring to FIG. 11a, in other embodiments, the first 71 and second 72 sources emit energy in first and second directions defining an angle γ of between more than 135 and 225 degrees, preferably between 160 and 200 degrees, more preferably between 175 and 185 degrees, most preferably about 180 degrees. In this most preferred embodiment, the emissions from the sources are substantially linear. Such a device would be useful for simultaneously treating adjacent vertebral bodies from the middle of the intervertebral disc, or from between adjacent vertebrae but outside the disc.

Figure 15A:
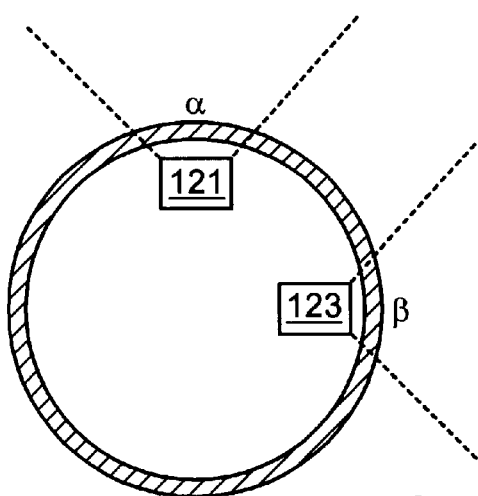
FIGS. 15a–15b disclose respectively a cross-section of a device of the present invention having sources which emit energy at different angles, and its operation within a disc.
Figure 15B:
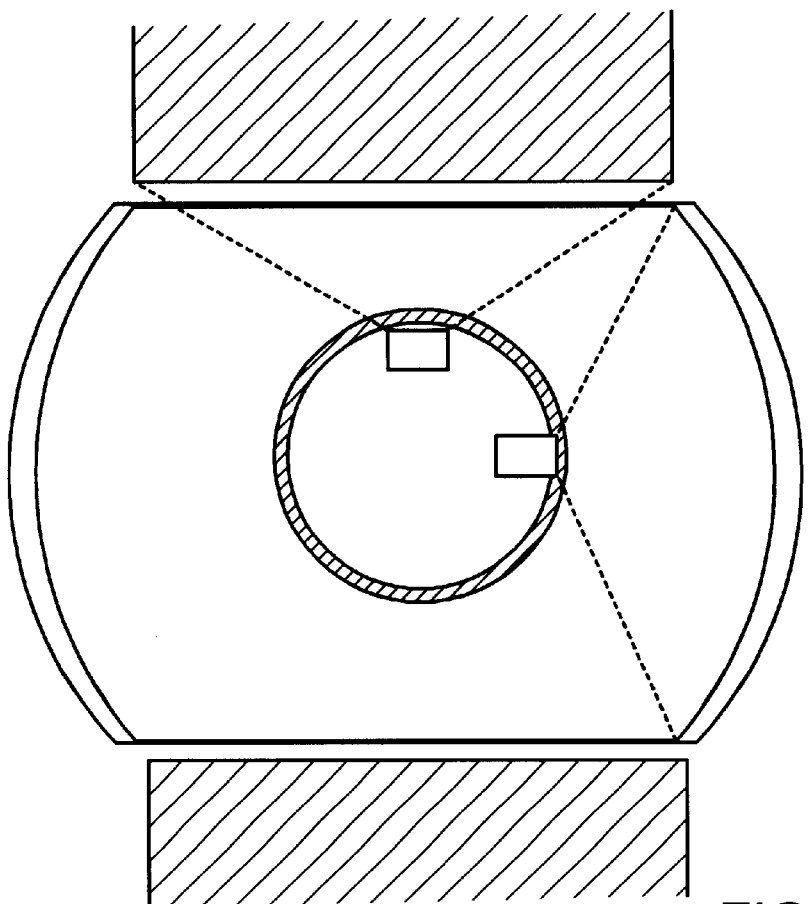

Now referring to FIGS. 15a and b, in some embodiments, first 121 and second 123 treatment sources have respective dispersion angles α and β, and wherein α is different than β. Such a device would be useful in simultaneously treating the endplates of a vertebral body and the walls of the annulus fibrosus from within the intervertebral disc, or from between adjacent vertebrae but outside the disc. In this particular design, since the endplates are relatively wide and the annulus fibrosus is relatively short, the wide angle a is preferably much greater than the angle β. In some embodiments, the wide angle α is at least 3 times greater than angle β, more preferably at least 10 times greater than angle β.

As noted above, Heggeness discloses a method of treating back pain which includes ablating the basivertebral nerve within the vertebral body portion of a vertebra. However, the Heggeness disclosure requires boring a hole in the vertebral body in order to gain unobstructed access to that nerve. Boring such a hole is undesirable because it is a time consuming process and leaves a hole in the treated vertebral body. In addition, the excavated bone must somehow be managed, thereby adding to the complexity of the procedure.

Therefore, also in accordance with the present invention, there is provided a method of denervating nerves in a vertebral body, comprising the steps of:
  a) providing a device having a treatment source,
  b) placing the treatment source inside the human body, and
  c) activating the treatment source to cause energy to flow from the treatment source and into the vertebral body in an amount sufficient to denervate nerves in the vertebral body.

In some embodiments, the treatment source is placed within the intervertebral disc. In other, it is placed between adjacent vertebrae but outside the disc. Preferably, the treatment source is an ultrasound transducer. Ultrasound is of particular advantage in this regard in that it can heat the vertebra from outside the vertebra. Accordingly, the time and invasiveness and bone management issues present in the method disclosed by Heggeness are avoided. Preferably, the ultrasonic transducer may be focused to provide localized energy substantially to an interior portion of the vertebral body, more preferably to an area housing the trunk of the basivertebral nerve. However, in some embodiments, the activation step causes energy to flow from the treatment source and substantially into the vertebral endplate in an amount sufficient to denervate a nerve ending in the vertebral endplate. In such instance, the treatment source need not necessarily be an ultrasound transducer.

In some embodiments which treat the vertebral body from within the intervertebral disc, the device is the device of FIG. 11a which provides essentially co-linear emission from the treatment sources, wherein the first and second sources are oriented so that the first source faces the upper adjacent vertebral endplate and the second source faces the lower adjacent vertebral endplate during step a) above. This method may further comprise the steps of:
  a) providing a device comprising first and second treatment sources forming a co-linear emision pattern,
  b) placing the treatment source into an intervertebral disc so that the first treatment source faces a first vertebral body and the second treatment source faces a second vertebral body, and
  c) activating the first treatment source to cause energy to flow from the first treatment source and into a first vertebral body in an amount sufficient to denervate a nerve in the first vertebral body, and.
  d) activating the second treatment source to cause energy to flow from the second treatment source and into the second vertebral body in an amount sufficient to denervate a nerve in the second vertebral body.

This device may then be rotated to treat the annulus fibrosus, so that the method may further include the steps of:
  e) rotating the device approximately 90° so that the first source faces a first portion of the annulus fibrosus, (and preferably the second source faces a second portion of the annulus fibrosus),
  f) energizing the first source and second source so that the first source heats the first portion of the annulus fibrosus and the second source heats the second portion of the annulus fibrosus.

In some embodiments, the treatment sequence is reversed so that this device first acts upon the annulus fibrosus, is rotated 90 degrees, and then acts upon the adjacent vertebral body or bodies.

In some embodiments, the device is the device of FIG. 7a which provides orthogonal emission from the treatment sources. In this case, the method of denervating nerves in a vertebral body comprises the steps of:

a) providing a device comprising first and second treatment sources forming an orthogonal emission pattern, b) placing the treatment source into an intervertebral disc so that the first treatment source faces a vertebral body and the second treatment source faces an annulus fibrosus, and c) activating the first treatment source to cause energy to flow from the first treatment source and into the vertebral body in an amount sufficient to denervate a nerve in the vertebral body, and.

d) activating the second treatment source to cause energy to flow from the second treatment source and into the first portion of the annulus fibrosus in an amount sufficient to denervate a nerve and/or shrink the collagen within the annulus fibrosus.

The device may then be rotated to treat the second adjacent vertebra and the opposing face of the annulus fibrosus, so that the method further comprises the steps of:

e) rotating the device approximately 90° so that the first source faces a second portion of the annulus fibrosus and the second source faces the second adjacent vertebra, f) activating the first treatment source to cause energy to flow from the first treatment source and into the second portion of the annulus fibrosus in an amount sufficient to denervate the nerves and/or shrink the collagen within the annulus fibrosus, and.

g) activating the second treatment source to cause energy to flow from the second treatment source and into the second vertebral body vertebral body in an amount sufficient to denervate the nerves in the second vertebral body.

h) energizing the first source so that the first source heats the first portion of the annulus fibrosus.

Figure 16A:
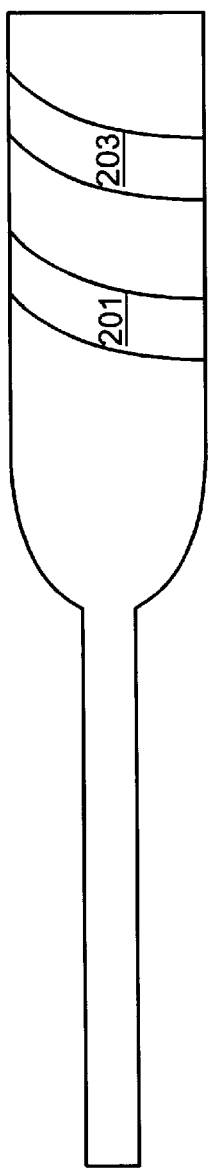
FIGS. 16a–16b discloses a cross-sectional view of a device of the present invention having radially symmetric sources, and its operation within a disc.
Figure 16B:
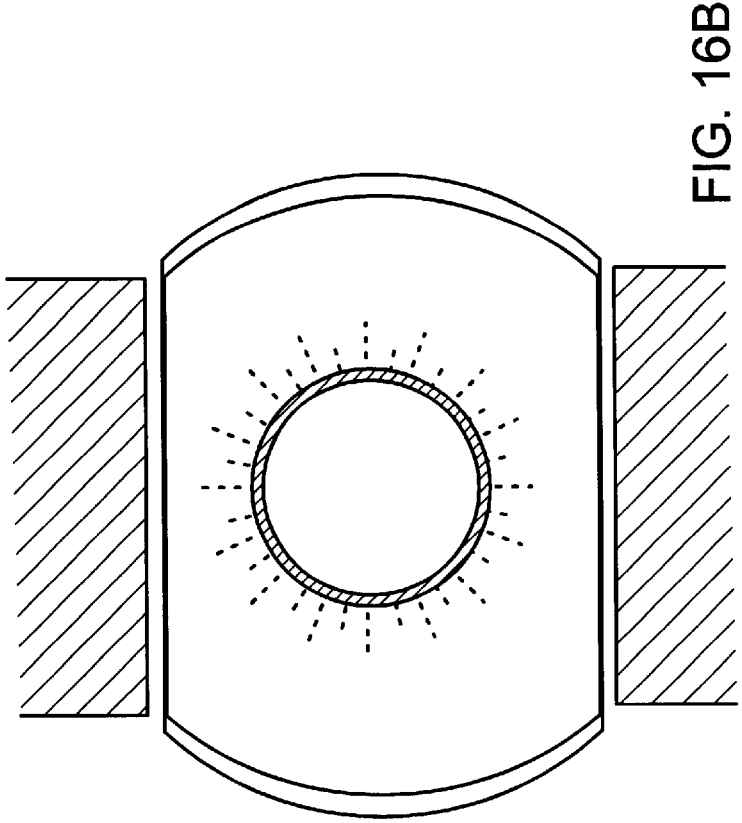
Figure 17:
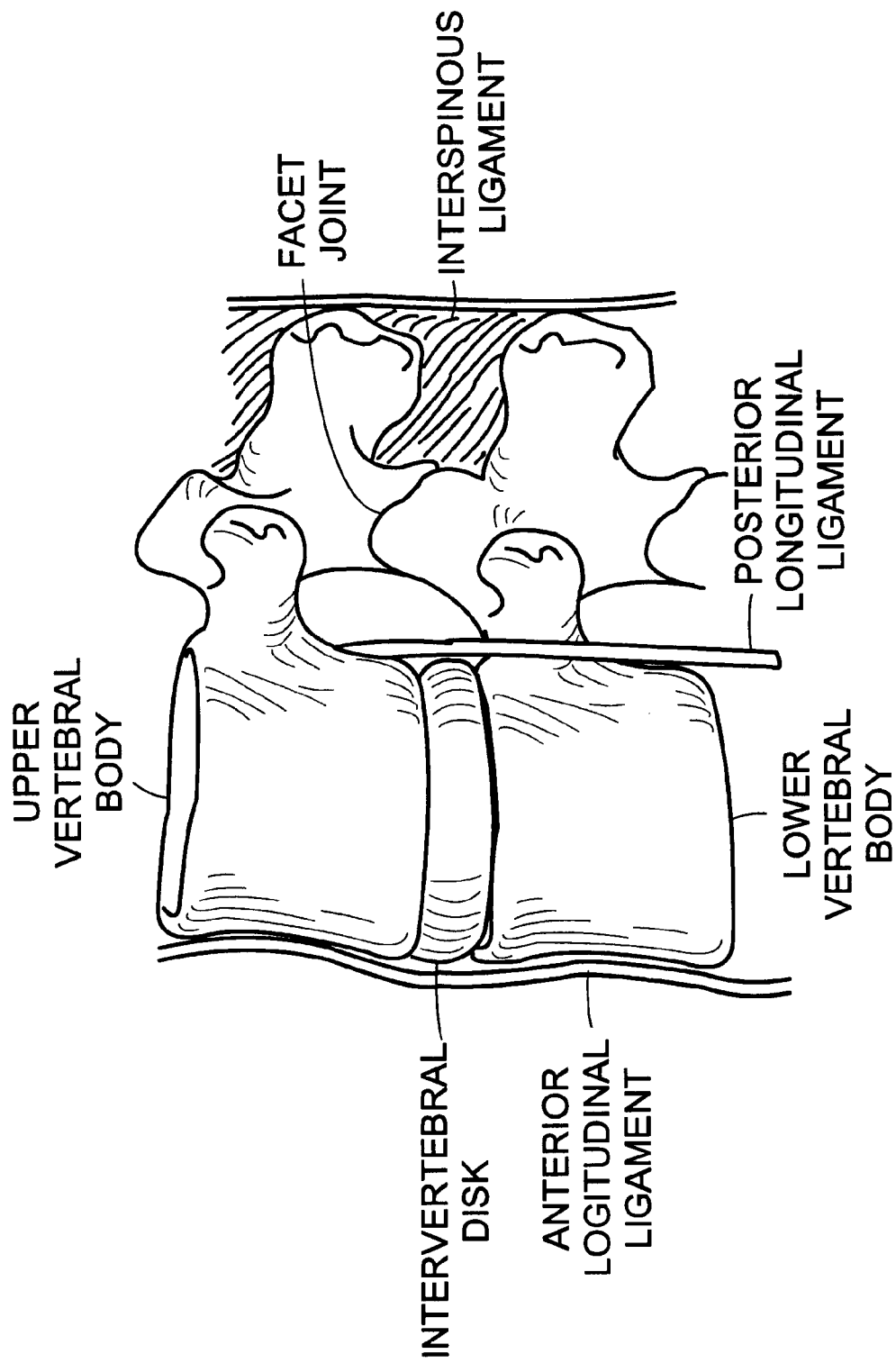
FIG. 17 is a cross sectional view of a conventional spine.

Although many embodiments of the present invention employ energy sources having preferred directional emissions, the present invention is not limited to preferred directional emissions. For example, and now referring to FIG. 16a, there is provided a probe have a first energy source 201 which spans the full circumference of the probe and provides a first radially uniform emission 309, and a second energy source 203 which spans the full circumference of the probe and provides a radially uniform emission 313. Now referring to FIG. 16b, when this probe is inserted into the disc, the first energy source may have a first frequency which preferentially couples with bone (and thereby preferentially heats the adjacent vertebral bodies), while the second energy source may have a second frequency which preferentially couples with collagen (and thereby preferentially heats the collagen in the annulus fibrosus).

As noted above, Heggeness discloses treating the nerves in bone with many different ablation sources, but does not disclose sources such as ultrasound, microwave, UV source, or an exothermic chemical source, each of which can act upon the nerve of interest from long range. Accordingly. Heggeness' procedure must bore into the vertebral body to a point near the nerve of interest in order to effect treatment. Cosman discloses treating only vertebral bodies which are tumorous, and so offers little help for the treatment of healthy vertebral bodies whose nerves may be the source of pain.

Therefore, in accordance with the present invention, there is provided a method of denervating nerves in a healthy vertebral body, comprising the steps of:

a) providing a device comprising at least one treatment source selected from the group consisting of an ultrasound transducer, a microwave source, a UV source, and a exothermic chemical source, b) placing the treatment source into the healthy vertebral body, and c) activating the device to cause energy to flow from the treatment source in an amount sufficient to denervate a nerve in the healthy vertebral body.

In some embodiments, the nerve of interest includes the trunk of the basivertebral nerve. In other embodiments, the nerve of interest includes a nerve ending located in the endplate portion of the vertebral body.

Because this inventive method allows the use of long range sources such as ultrasonic energy as a way of heating, it can focus energy from a far away location. Therefore, the method does not require that the treatment source be placed in close proximity to the nerve of interest. Therefore, this method is advantageous if a) the approach to a nerve of known location is problematic, b) if the location of the nerve is not well known, c) if the surgeon desires to heat either the entire vertebral body or just the nerves of the vertebral endplate. However, care must be taken to select an appropriate frequency which allows sufficient energy transmission through the vertebral body.

As noted above, both Heggeness and Cosman discloses treating the nerves in bone with many different treatment sources, but do not disclose treatment sources which effect environmental cooling.

Therefore, in accordance with the present invention, there is provided a method of denervating nerves in a healthy vertebral body, comprising the steps of:

a) providing a device comprising a cooling source, b) placing the cooling source in the healthy vertebral body, and c) activating the device to cool the healthy vertebral body in an amount sufficient to denervate the nerves in the healthy vertebral body.

In one embodiment, the cooling source comprises liquid nitrogen. In another, the cooling source comprises heat pipe technology.

The many conventional methods for heating the annulus fibrosus or nucleus pulposus disclose essentially direct methods of heating these tissues. Unfortunately, due to the low heat capacity of these tissues, the heat imparted to them dissipates relatively quickly, thereby leading to relatively short treatment times and relatively localized treatment.

Therefore, in accordance with the present invention, there is provided a method of treating an intervertebral disc, comprising the steps of:

a) providing a device comprising at least one ultrasound transducer, b) placing the ultrasound transducer into the human body, and c) energizing the ultrasound transducer to cause energy to flow from the energy output source and into the vertebral endplate in an amount sufficient to heat the vertebral endplate to a temperature which causes heat transfer from the vertebral endplate to the intervertebral disc in an amount sufficient to cause at least one of collagen shrinkage or nerve denervation within the intervertebral disc.

In this inventive method, the vertebral endplate acts as a heat capacitor. This provides two advantages. First, the heat in the vertebral endplate spreads evenly over the endplate, thereby providing a uniform heating source which spans the width of the annulus fibrosus. Second, the high heat capacity of the vertebral body allows it to effectively conduct and/or radiate heat for a relatively long period of time. Thereby allowing for prolonged treatment of the annulus fibrosus.

In some embodiments, this method comprises the step of:

a) energizing an ultrasound transducer to cause energy to flow from the ultrasound transducer and into the vertebral endplate in an amount sufficient to heat the vertebral endplate to a temperature which causes heat transfer from the vertebral endplate to the intervertebral disc in an amount sufficient to cause at least one of collagen shrinkage or nerve denervation within the intervertebral disc.

In other embodiments, the device is an implant. These implants have the advantage of requiring only a single invasive procedure. Since it is believed that many of the energetic treatments, such as material removal, provide only temporary relief to the patient, providing an implant having a treatment sources which can be activated from outside the body provides a distinct advantage over conventional probe-based technologies which require invasive procedure for each treatment.

Accordingly, the implant is shaped for substantially permanent residence within the human body. When the implant is placed within the intervertebral disc, it preferably has a height which is less than the height of the disc. Also preferably, it has a foot print which is less than the foot print of the disc. Also preferably, the width of the implant is less than the width of the disc. In some instances, the implant is shaped to substantially reside within the space occupied by the nucleus pulposus.

Therefore, in some embodiments, the step of therapeutically treating comprises the steps of:

a) placing an implant comprising a treatment source substantially completely within the human body (preferably, within the disc, more preferably within the nucleus pulposus), and b) activating the treatment source to treat a first tissue site.

We claim:

1. A device for therapeutically treating back or leg pain, comprising:
    a) a probe having a proximal portion and a distal portion,
    b) first and second treatment sources, each source located in the distal portion of the probe,
wherein the first treatment source is adapted to therapeutically treat a first tissue site, the second treatment source is adapted to therapeutically treat a second different tissue site, wherein the first and second sources each have a surface energy flux, and the surface energy flux of the first source is different than the surface energy flux of the second source, wherein the surface energy flux of the first source is at least twice as large as the surface energy flux of the second source,
wherein the first and second sources emit energy in first and second directions, the directions defining an angle therebetween of between 45 and 135 degrees, and
wherein the first and second different tissue sites are selected from the group consisting of:
    i) a first intervertebral disc, and
    ii) a first vertebra.

2. The device of claim 1 wherein each of the first and second treatment sources comprise ultrasound transducers.

3. The device of claim 2 wherein each transducer is individually controllable.

4. The device of claim 1 wherein the first and second sources each have a surface flux density, and the surface flux density of the first source is different than the surface flux density of the second source.

5. The device of claim 4 wherein the surface flux density of the first source is twice as large as the surface flux density of the second source.

6. The device of claim 1 wherein the angle is between 80 and 100 degrees.

7. The device of claim 1 wherein at least one of the first and second treatment sources comprises a microwave source.

8. A device for therapeutically treating back or leg pain, comprising:
    a) a probe having a proximal portion and a distal portion,
    b) first and second treatment sources, each source located in the distal portion of the probe,
wherein the first treatment source is adapted to therapeutically treat a first tissue site, the second treatment source is adapted to therapeutically treat a second different tissue site, wherein the first and second sources each have a surface energy flux, and the surface energy flux of the first source is different than the surface energy flux of the second source, wherein the first and second sources have respective emission angles $\alpha$ and $\beta$, and
wherein $\alpha$ is different than $\beta$, wherein the first and second sources emit energy in first and second directions, the directions defining an angle therebetween of between 135 and 225 degrees and
wherein the first and second different tissue sites are selected from the group consisting of:
    i) a first intervertebral disc,
    ii) a first vertebra,
    iii) a first spinal ligament, and
    iv) a first spinal facet joint capsule,
    v) a second intervertebral disc,
    vi) a second vertebra,
    vii) a second spinal ligament, and
    viii) a second spinal facet joint capsule.

9. The device of claim 8 wherein the angle is between 160 and 200 degrees.

10. The device of claim 8 wherein the angle is between 175 and 185 degrees.

11. A device for therapeutically treating back or leg pain, comprising:
    a) a probe having a proximal portion and a distal portion,
    b) first and second treatment sources, each source located in the distal portion of the probe,
wherein the first treatment source is adapted to therapeutically treat a first tissue site, the second treatment source is adapted to therapeutically treat a second different tissue site, wherein the first and second sources each have a surface energy flux, and the surface energy flux of the first source is different than the surface energy flux of the second source, and
wherein the first and second different tissue sites are selected from the group consisting of:
    i) a first intervertebral disc,
    ii) a first vertebra,
    iii) a first spinal ligament, and
    iv) a first spinal facet joint capsule,
    v) a second intervertebral disc, vi) a second vertebra, vii) a second spinal ligament, and viii) a second spinal facet joint capsule, and wherein the first and second sources respectively comprise first and second ultrasound transducers respectively having first and second ceramic component compositions, and the first ceramic component composition is different than the second ceramic component composition.

12. A device for therapeutically treating back or leg pain, comprising:

a) a probe having a proximal portion and a distal portion, b) first and second treatment sources, each source located in the distal portion of the probe, wherein the first treatment source is adapted to therapeutically treat a first tissue site, the second treatment source is adapted to therapeutically treat a second different tissue site, wherein the first and second sources each have a surface energy flux, and the surface energy flux of the first source is different than the surface energy flux of the second source, and wherein the first and second different tissue sites are selected from the group consisting of:

i) a first intervertebral disc, ii) a first vertebra, iii) a first spinal ligament, and iv) a first spinal facet joint capsule, v) a second intervertebral disc, vi) a second vertebra, vii) a second spinal ligament, and viii) a second spinal facet joint capsule, and wherein the first and second sources respectively comprise first and second ultrasound transducers respectively having first and second ceramic components, and the first ceramic component has a first wall thickness and the second ceramic component has a second wall thickness, and the first wall thickness is different than the second wall thickness, wherein the first thickness is at least 20% greater than the second thickness.

13. A device for therapeutically treating back or leg pain, comprising:

a) a probe having a proximal portion and a distal portion, b) first and second treatment sources, each source located in the distal portion of the probe, wherein the first treatment source is adapted to therapeutically treat a first tissue site, the second treatment source is adapted to therapeutically treat a second different tissue site, wherein the first and second sources each have a surface energy flux, and the surface energy flux of the first source is different than the surface energy flux of the second source, and wherein the first and second different tissue sites are selected from the group consisting of:

i) a first intervertebral disc, ii) a first vertebra, iii) a first spinal ligament, and iv) a first spinal facet joint capsule, v) a second intervertebral disc, vi) a second vertebra, vii) a second spinal ligament, and viii) a second spinal facet joint capsule, and wherein the first and second sources respectively comprise first and second ultrasound transducers having first and second ceramic components, wherein the first ceramic component has a first coating thereon and the second ceramic component has a second coating thereon, and the first coating is different than the second coating.

14. A device for therapeutically treating back or leg pain, comprising:

a) a probe having a proximal portion and a distal portion, b) first and second treatment sources, each source located in the distal portion of the probe, wherein the first treatment source is adapted to therapeutically treat a first tissue site, the second treatment source is adapted to therapeutically treat a second different tissue site, wherein the first and second sources each have a surface energy flux, and the surface energy flux of the first source is different than the surface energy flux of the second source, and wherein the first and second different tissue sites are selected from the group consisting of:

i) a first intervertebral disc, ii) a first vertebra, iii) a first spinal ligament, and iv) a first spinal facet joint capsule, v) a second intervertebral disc, vi) a second vertebra, vii) a second spinal ligament, and viii) a second spinal facet joint capsule, and further comprising:

c) a third treatment source located at the distal portion of the probe, wherein the third treatment source is adapted to treat a third tissue site having the same tissue structure as the first tissue site.

15. The device of claim 14 further comprising:

d) a fourth treatment source located in the distal portion of the probe, wherein the fourth treatment source is adapted to treat a fourth tissue site having the same tissue structure as the second tissue site.

16. The device of claim 15 wherein the first, second, third and fourth sources emit energy in first, second, third and fourth directions, the directions respectively defining an angle $\gamma$ between the first and second directions, an angle $\delta$ between the first and third direction, and an angle $\epsilon$ between the first and fourth directions, wherein angle $\gamma$ is between 80 and 100 degrees, angle $\delta$ is between 170 and 190 degrees, angle $\epsilon$ is between 260 and 280 degrees.

17. A method of treating an intervertebral disc, comprising the steps of:

a) providing a device comprising an energy output source, b) placing the energy output source into the human body, and c) energizing the energy output source to cause energy to flow from the energy output source and into a vertebral endplate in an amount sufficient to heat the vertebral endplate to a temperature which causes heat transfer from the vertebral endplate to the intervertebral disc in an amount sufficient to cause at least one of collagen shrinkage or nerve denervation within the intervertebral disc.

18. The method of claim 17 wherein the energy output source is an ultrasound transducer.

19. The method of claim 17 wherein the energy output source is an RF source.

20. A method of treating back or leg pain, comprising the step of therapeutically treating first and second different tissue sites with a single device, each tissue site being selected from the group consisting of:

i) a first intervertebral disc,
ii) a first vertebra,
iii) a first spinal ligament,
iv) a first spinal facet joint capsule,
v) a second intervertebral disc,
vi) a second vertebra,
vii) a second spinal ligament, and
viii) a second spinal facet joint capsule.

21. The method of claim 20 wherein the device comprises a probe having first and second treatment sources, and wherein the step of therapeutically treating comprises the steps of:
   a) placing the device at least partially within the human body,
   b) activating the first treatment source to treat the first tissue site,
   c) activating the second treatment source to treat the second tissue site, and,
   d) withdrawing the device from the human body.

22. The method of claim 21 wherein step a) comprises placing the device into an intervertebral disc.

23. The method of claim 21 wherein step a) comprises placing the device between adjacent first and second vertebrae and outside an intervertebral disc therebetween.

24. The method of claim 21 wherein step a) comprises placing the device into a vertebral body portion of the first vertebra.

25. The method of claim 20 wherein the device is an implant comprising first and second treatment sources, and the step of therapeutically treating comprises the steps of:
   a) placing the implant substantially completely within the human body,
   b) activating the first treatment source to treat the first tissue site,
   c) activating the second treatment source to treat the second tissue site.

26. The method of claim 20 wherein the first tissue site is the first intervertebral disc.

27. The method of claim 26 wherein the step of therapeutically treating the first intervertebral disc comprises coagulating collagen within the disc.

28. The method of claim 26 wherein the step of therapeutically treating the first intervertebral disc comprises denervating at least a portion of a nerve within the disc.

29. The method of claim 26 wherein the step of therapeutically treating the first intervertebral disc comprises removing mass from within the disc.

30. The method of claim 20 wherein the first tissue site is the first vertebra.

31. The method of claim 30 wherein the step of therapeutically treating the first vertebra comprises denervating at least a portion of a basivertebral nerve within a vertebral body portion of the first vertebra.

32. The method of claim 20 wherein the first tissue site is the first vertebra and the second tissue site is the second vertebra.

33. The method of claim 20 wherein the first tissue site is the first intervertebral disc and the second tissue site is the second intervertebral disc.

34. The method of claim 20 wherein the first tissue site is the first spinal ligament, and the step of therapeutically treating the first spinal ligament comprises denervating a nerve within the first spinal ligament.

35. The method of claim 20 wherein the first tissue site is the first spinal ligament, and the step of therapeutically treating the first spinal ligament comprises shrinking collagen within the first spinal ligament.

36. The method of claim 20 wherein the first tissue site is the first spinal facet joint capsule.

37. The method of claim 36 wherein the step of therapeutically treating the first spinal facet joint capsule comprises denervating a nerve within the capsule.

38. The method of claim 36 wherein the step of therapeutically treating the first spinal facet joint capsule comprises shrinking a collagenous ligament of the capsule.

39. The method of claim 20 wherein the first tissue site is the first intervertebral disc and the second tissue site is the first vertebra.

40. The method of claim 39 wherein the step of therapeutically treating comprises heating an annulus fibrosus portion of the first intervertebral disc and denervating at least a portion of a basivertebral nerve located in the first vertebra.

41. The method of claim 40 further comprising the step of b) removing at least a portion of a nucleus pulposus located within the disc.

42. The method of claim 41 wherein the step of removing at least a portion of the nucleus pulposus includes the step of liquifying the nucleus pulposus.

43. The method of claim 20 wherein the first tissue site is the first intervertebral disc and the second tissue site is the first spinal ligament.

44. The method of claim 20 wherein the first tissue site is the first spinal facet joint capsule, and the second tissue site is the second spinal facet joint capsule.

45. The method of claim 20 wherein the first tissue site is the first vertebra and the second tissue site is the first spinal ligament.

46. The method of claim 20 wherein the first tissue site is the first spinal ligament, and the second tissue site is the second spinal ligament.

47. A method of treating back or leg pain, comprising the step of therapeutically treating first and second components within an intervertebral disc with a single device.

48. The method of claim 47, wherein the treatment occurs simultaneously.

49. The method of claim 47, wherein the treatment occurs sequentially.

50. The method of claim 47 wherein the first component is within an annulus fibrosus within the intervertebral disc, and the second component is within a nucleus pulposus within the intervertebral disc.

51. The method of claim 47 wherein the first component is an interior component of the intervertebral disc, and the second component is an surface component of the intervertebral disc.

52. A method of treating back or leg pain, comprising the step of therapeutically treating first and second different components within a vertebra with a single device.

53. The method of claim 52, wherein the treatment occurs simultaneously.

54. The method of claim 52, wherein the treatment occurs sequentially.

55. The method of claim 52, wherein the first component is at least a portion of a basivertebral nerve trunk located within a cancellous bone portion of a vertebral body portion of the vertebra, and
the second component is at least a portion of a nerve ending located within an endplate portion of a vertebral body portion of the vertebra.

56. A method of treating back or leg pain, comprising the step of therapeutically treating first and second different components within a spinal facet joint capsule with a single device.

57. The method of claim 56, wherein the treatment occurs simultaneously.

58. The method of claim 56, wherein the treatment occurs sequentially.

59. The method of claim 56, wherein the first component is a loose collagen fiber portion of a ligament within the capsule, and the second component is a nerve fibril within a cartilagenous endplate of the capsule.

60. A method of treating back or leg pain, comprising the step of therapeutically treating first and second vertebral bodies with a single device.

61. The method of claim 60, wherein the treatment occurs simultaneously.

62. The method of claim 60, wherein the treatment occurs sequentially.

63. The method of claim 60, wherein the treatment therapeutically treats at least a portion of a basivertebral nerve trunk located within a cancellous bone portion of the first vertebral body, and a nerve ending ending located within an endplate bone portion of the second vertebral body.

64. The method of claim 60, wherein the treatment therapeutically treats at least a portion of a basivertebral nerve trunk located within a cancellous bone portion of the first vertebral body, and at least a portion of a basivertebral nerve ending located within a cancellous bone portion of the second vertebral body.

65. The method of claim 60, wherein the treatment therapeutically treats at least a portion of a basivertebral nerve ending located within an endplate portion of the first vertebral body, and a basivertebral nerve ending located within an endplate bone portion of the second vertebral body.

66. A method of thermally treating a bony tissue site and a soft tissue site, comprising the steps of:
   a) providing a device having first and second treatment sources,
   b) placing the treatment sources into a target site within the human body,
   activating the device to cause the first treatment source to therapeutically heat the bony tissue site, and to cause the second treatment source to therapeutically heat the soft tissue site.

67. The method of claim 66 wherein the bony tissue site is a vertebral body and the soft tissue site is an intervertebral disc.

68. The method of claim 67 wherein the first energy output source is an RF source.

69. The method of claim 68 wherein the second energy output source is an ultrasound source.

70. The method of claim 67 wherein each treatment source is an ultrasound transducer, and the first treatment source emits less ultrasound energy than the second treatment source.

71. The method of claim 70 wherein the first treatment source is directed to a vertebral endplate, and the second treatment source is directed to an annulus fibrosus.

72. The method of claim 66 wherein the bony tissue site is a vertebra, the soft tissue site is an intervertebral disc, the first energy output source is an RF source, and the second energy output source is an ultrasound source.

73. A device for therapeutically treating back or leg pain, comprising:
   a) a probe having a proximal portion and a distal portion,
   b) first and second treatment sources, each source located in the distal portion
   of the probe and adapted to therapeutically treat at least a first tissue site,
   wherein the first treatment source provides therapy by a form of energy which is different than that of the second treatment source,
   wherein the first treatment source is an ultrasonic transducer and the second treatment source is a resistive heating element.

74. A device for therapeutically treating back or leg pain, comprising:
   a) a probe having a proximal portion and a distal portion,
   b) first and second treatment sources, each source located in the distal portion
   of the probe and adapted to therapeutically treat at least a first tissue site,
   wherein the first treatment source provides therapy by a form of energy which is different than that of the second treatment source, wherein the first treatment source is an energy source and the second treatment source is a chemical delivery source.

75. The device of claim 74 wherein the energy source is an ultrasound transducer.

76. The device of claim 74 wherein the chemical delivery source is a source which delivers a pair of chemicals which when combined have an exothermic reaction.

* * * * *